United States Patent [19]

Jackson et al.

[11] Patent Number: 5,613,973
[45] Date of Patent: Mar. 25, 1997

[54] LARAPOSCOPIC SURGICAL GRASPER HAVING AN ATTACHABLE STRAP

[75] Inventors: Robert C. Jackson, Clarence; Thomas W. Klementowski, Amherst; Jack A. Belstadt, North Tonawanda, all of N.Y.

[73] Assignee: Wilson Greatbatch Ltd., Clarence, N.Y.

[21] Appl. No.: 402,344

[22] Filed: Mar. 10, 1995

[51] Int. Cl.$^6$ ............................ A61B 11/24; A61B 11/26
[52] U.S. Cl. ........................................ 606/113; 606/1
[58] Field of Search ................................ 606/113, 114, 606/106–110, 127, 128; 119/803, 804, 802

[56] References Cited

U.S. PATENT DOCUMENTS

| | | | |
|---|---|---|---|
| 480,870 | 8/1892 | Harris | 606/113 |
| 668,647 | 2/1901 | Jaenicke . | |
| 974,879 | 11/1910 | Gwinn | 606/113 |
| 1,461,864 | 12/1919 | Day . | |
| 1,470,914 | 6/1921 | Day . | |
| 2,054,149 | 3/1935 | Wappler | 128/309 |
| 3,181,533 | 1/1962 | Heath | 128/320 |
| 3,828,790 | 8/1974 | Curtiss et al. | 128/320 |
| 3,835,859 | 9/1974 | Roberts et al. | 606/113 |
| 3,903,892 | 9/1975 | Komiya | 128/303.15 |
| 4,592,355 | 6/1986 | Antebi | 128/326 |
| 5,084,054 | 1/1992 | Bencini et al. | 606/113 |
| 5,098,440 | 3/1992 | Hillstead | 606/108 |
| 5,106,369 | 4/1992 | Christmas | 604/51 |
| 5,108,406 | 4/1992 | Lee | 606/106 |
| 5,163,942 | 11/1992 | Rydell | 606/113 |
| 5,312,416 | 5/1994 | Spaeth et al. | 606/114 |
| 5,376,094 | 12/1994 | Kline | 606/113 |
| 5,387,219 | 2/1995 | Rappe | 606/113 |
| 5,417,684 | 5/1995 | Jackson et al. | 606/113 |
| 5,486,183 | 1/1996 | Middleman et al. | 606/127 |

*Primary Examiner*—Robert A. Hafer
*Assistant Examiner*—Justine Yu
*Attorney, Agent, or Firm*—Hodgson, Russ, Andrews, Woods & Goodyear LLP

[57] ABSTRACT

A medical grasper device (10) that is useful for holding and manipulating a body organ is described. The grasper device is partially inserted into a body cavity and comprises a flexible strap (14) having a distal section (18) that is deployed from a tube (12) to form a partial closed loop (2). A terminal end of the strap has an aperture (42) that is manipulated by a separate forceps-type device to mate with a connection means (56) provided on the grasper device to complete the loop. The closed loop is then adjustable in size to provide for positioning the loop at a desired location around the target body organ to hold and manipulate the body organ. At such time as the grasper device is no longer needed in the surgical procedure, the strap is either removed from the connection means with the aforementioned forceps-type device or is cut by a separate cutting means to release the loop from the body organ and the grasper device is removed from the body cavity.

51 Claims, 6 Drawing Sheets

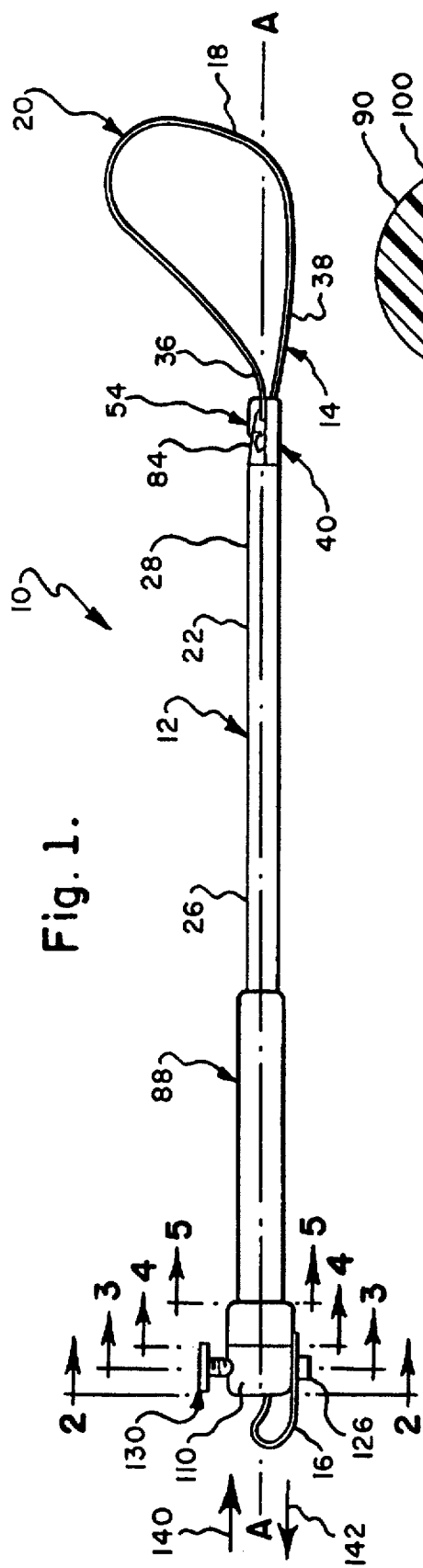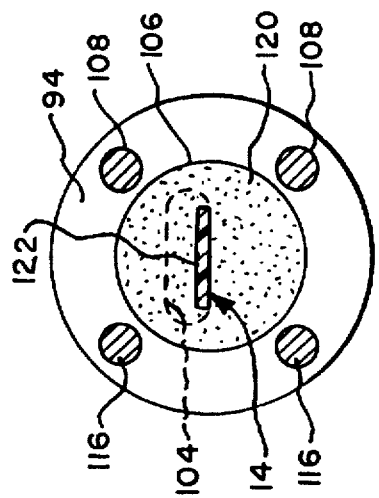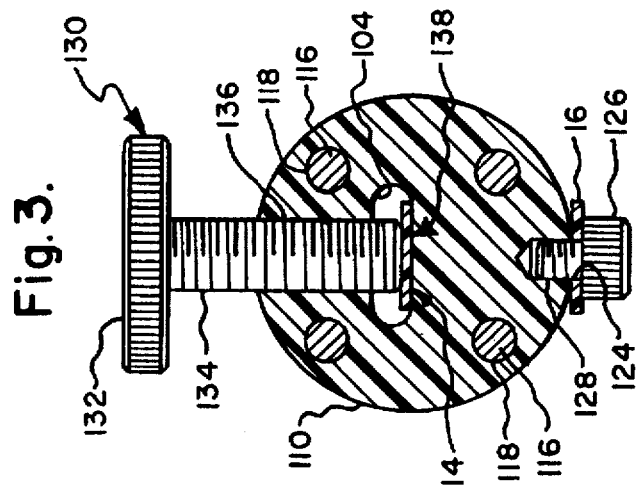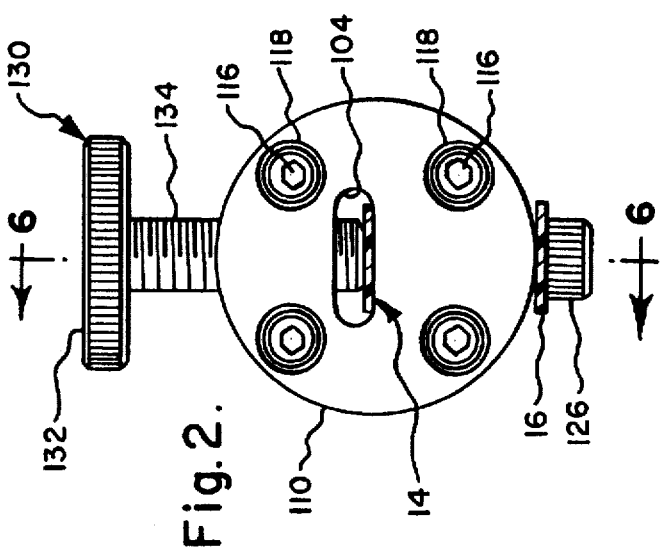

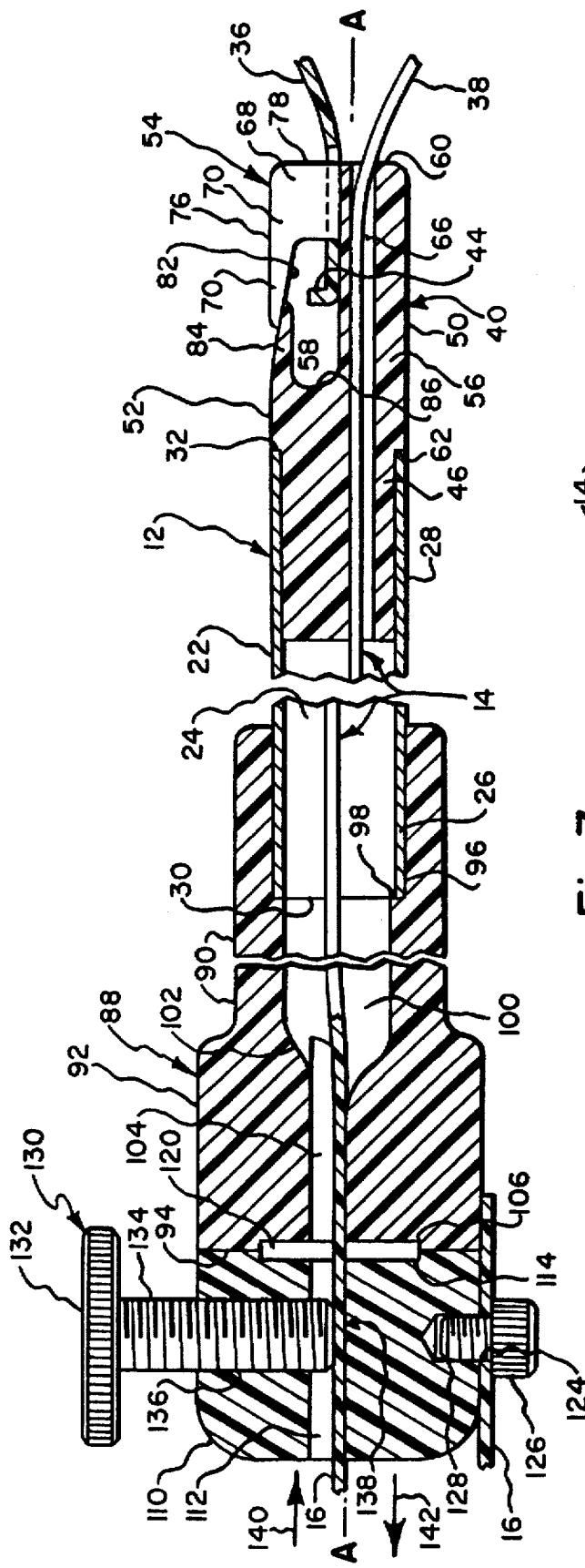
Fig. 6.
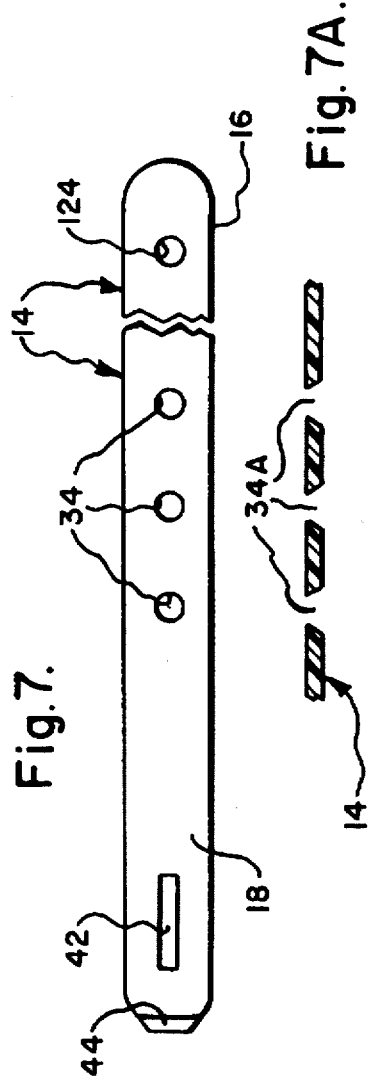
Fig. 7.
Fig. 7A.
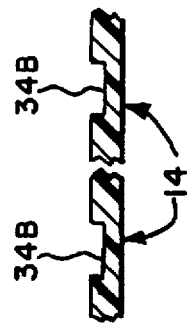
Fig. 7B.

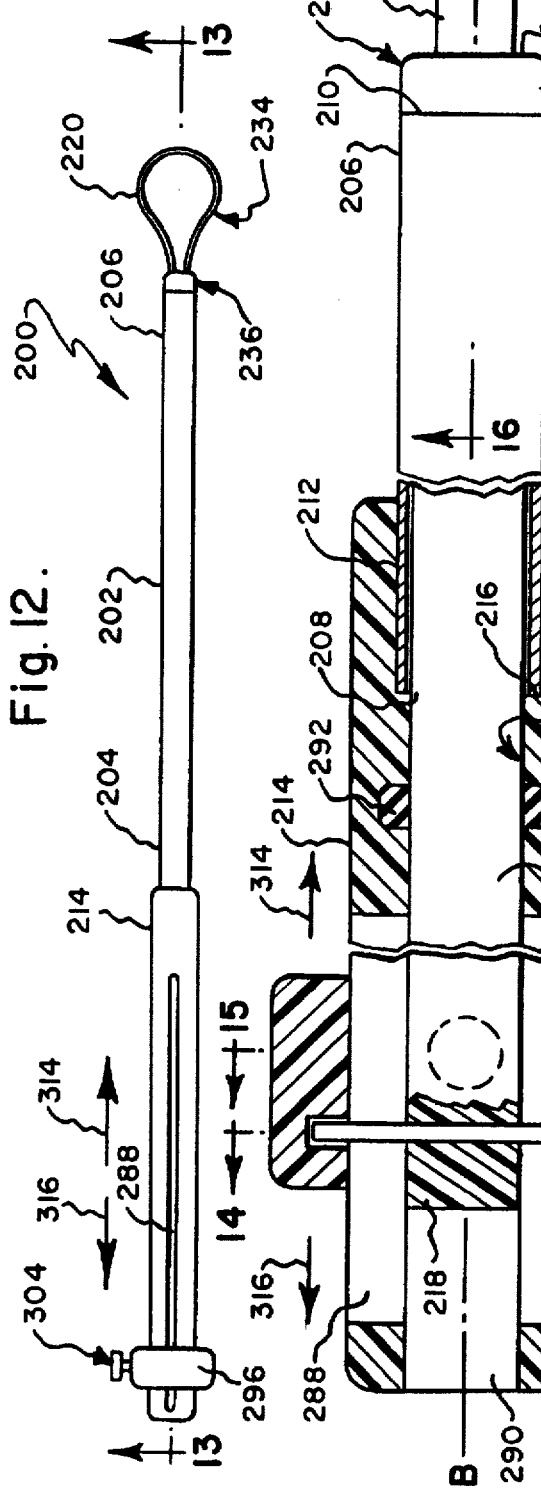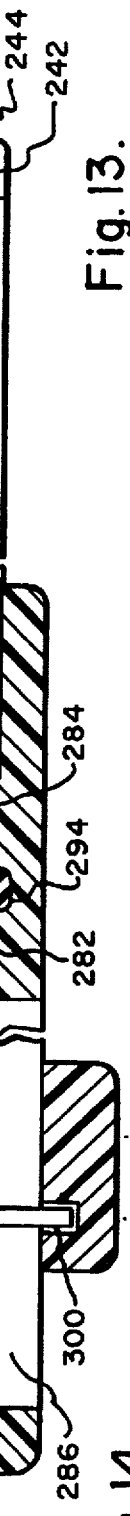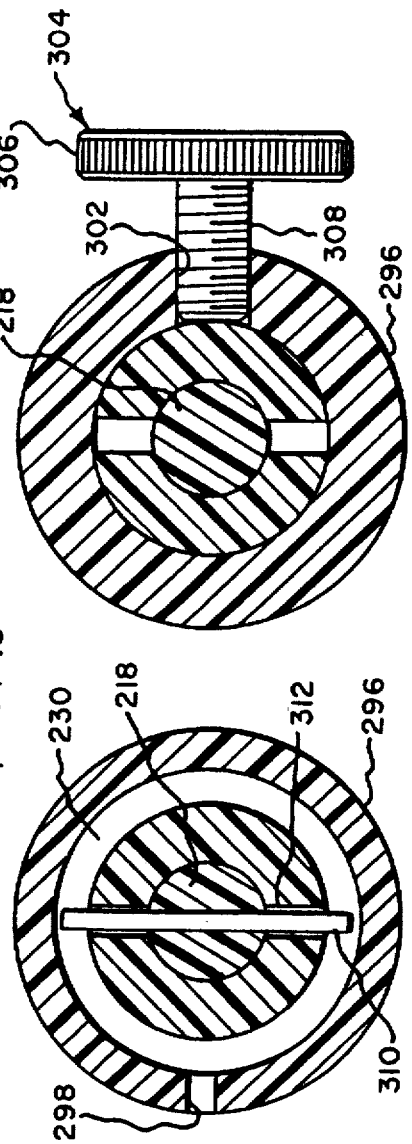

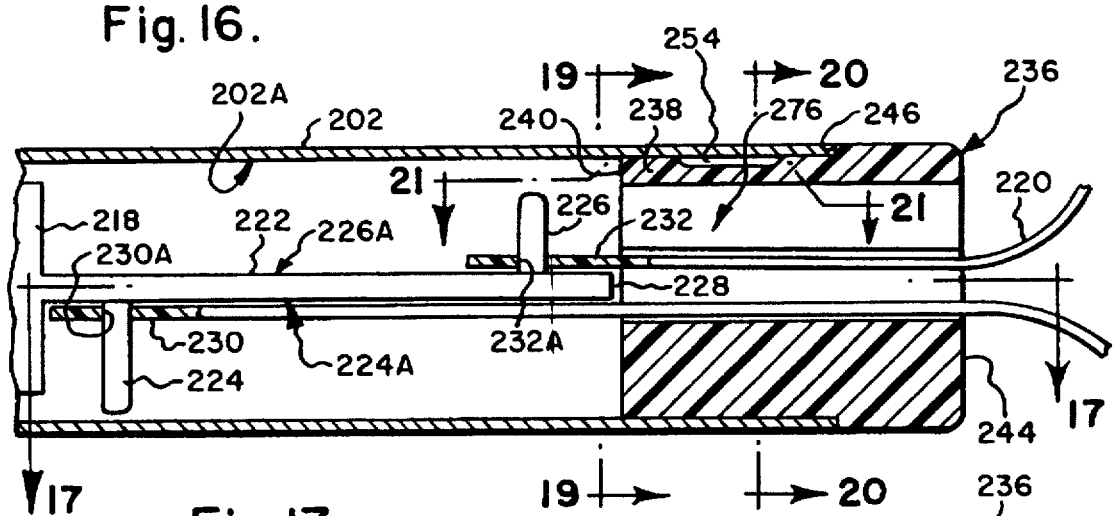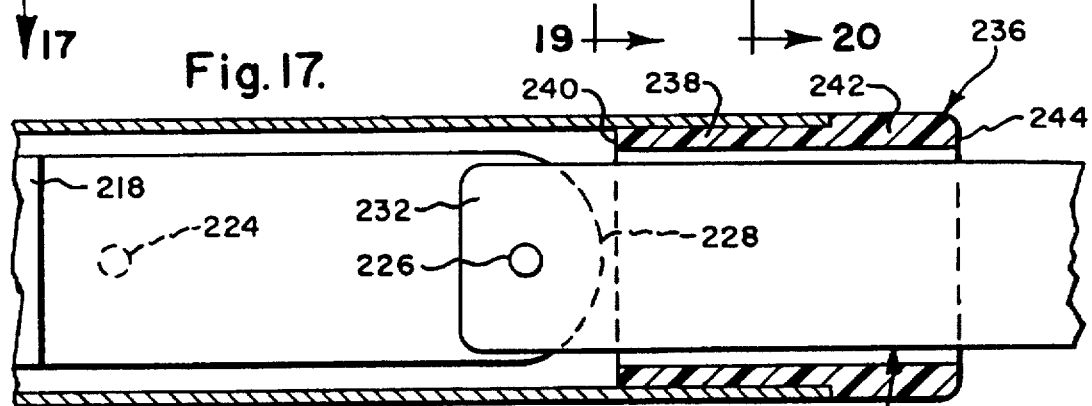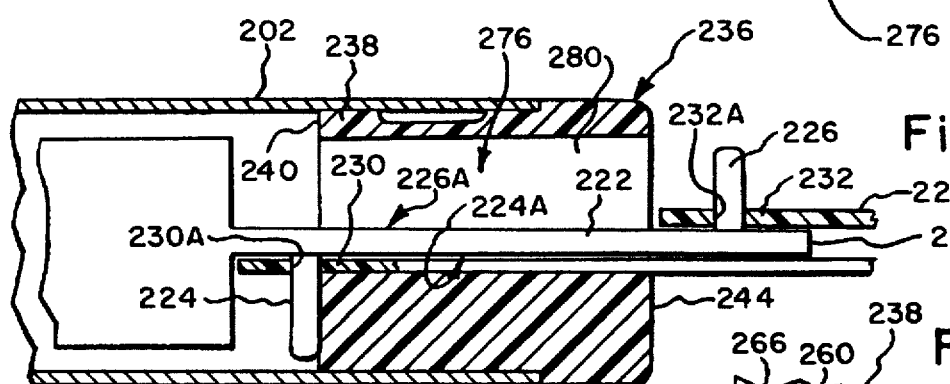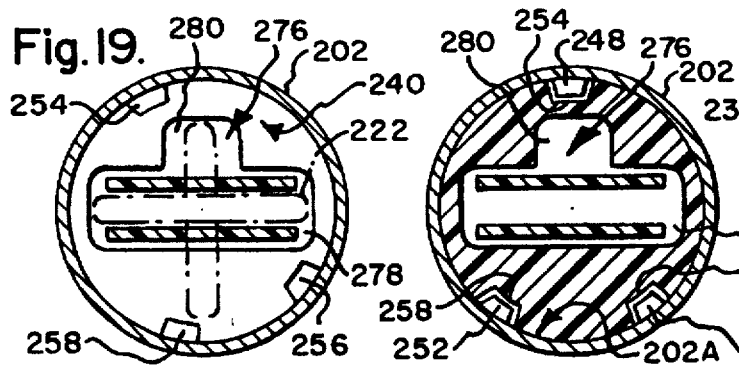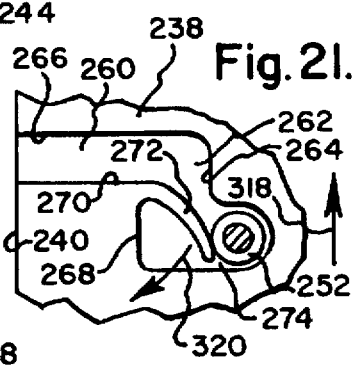

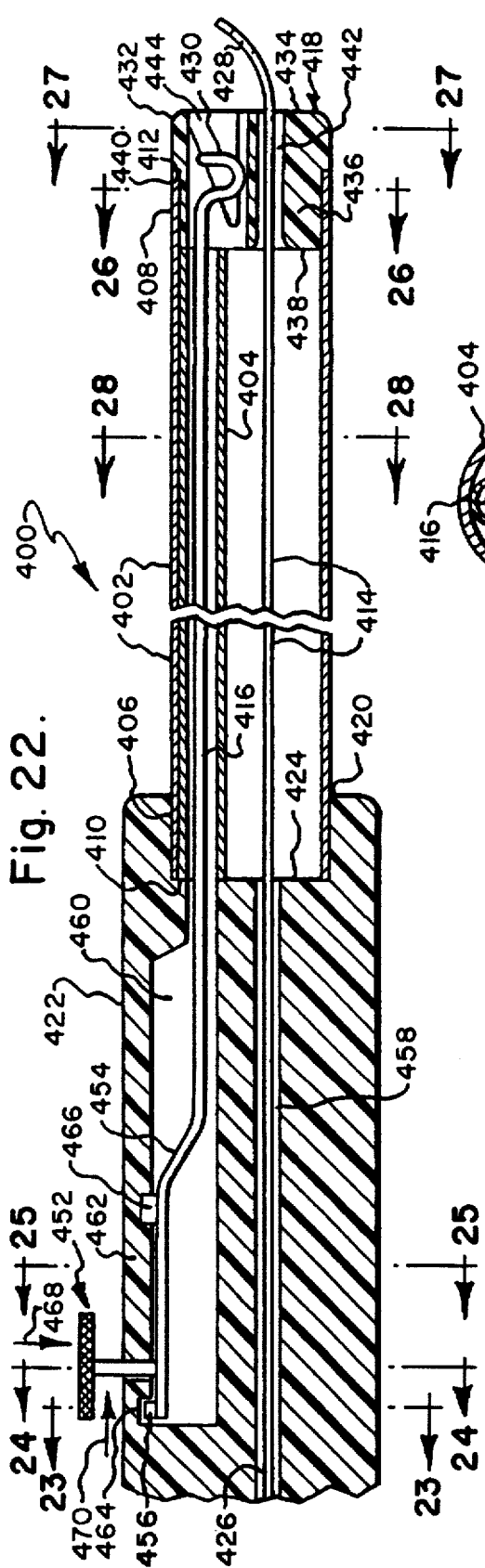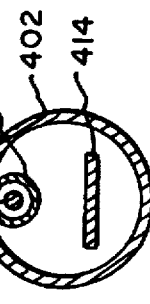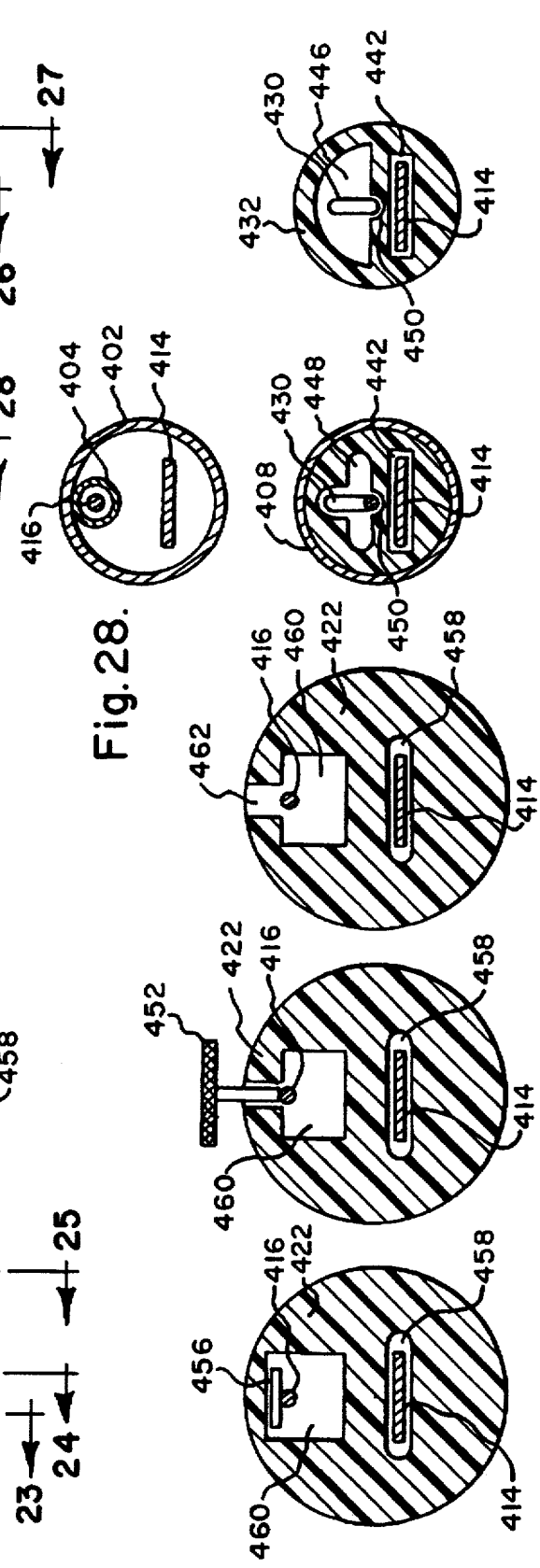

LARAPOSCOPIC SURGICAL GRASPER HAVING AN ATTACHABLE STRAP

BACKGROUND OF THE INVENTION

1. Field of the Invention

The present invention generally relates to a medical device and more particularly to a grasper device that is useful for holding and manipulating a body organ during a laparoscopic surgical procedure. More specifically, the grasper device of the present invention has a manipulative means and a strap that is manipulatable around a body organ, particularly the type that is connected to adjoining tissue at both ends such as the colon. The strap is then attachable or reattachable to 2nd detachable from a strap connection means provided either on the conduit means or the manipulative means to encircle the body organ. This enables a surgeon to move the body organ as needed during the laparoscopic surgical procedure.

Given the current trend to reducing patient trauma as much as possible by performing operative procedures that are less invasive and less traumatic to the patient and the subject body organ, laparoscopic surgical procedures are being performed with increasing frequency. Laparoscopic surgery is a form of abdominal surgery using a laparoscope and other surgical instruments introduced into the abdomen through separate cannula ports. A laparoscope is an instrument for visualizing the interior of the abdomen and the various body organs contained therein. In laparoscopic surgery, the laparoscope is introduced into a body cavity such as the abdomen through a cannula port fitted to a trocar, which is a sharp pointed instrument that is punctured through the body cavity wall to insert the cannula. The grasper device of the present invention is introduced into the body cavity through a separate cannula port where it is used to hold and manipulate a body organ and/or body tissue attached to adjoining body tissue at both ends during the surgery in a non-slip and atraumatic engagement. Additional cannula ports are used for other surgical instruments needed for the surgical procedure.

2. Prior Art

The advent of laparoscopic surgery has fostered the rapid development of improved surgical methods and concomitant advancements in instruments that are useful to a surgeon performing the surgery.

U.S. Pat. No. 5,106,369 to Christmas describes an umbilical cord stabilizer comprising a wire which is normally housed inside a surgical needle. The needle is introduced into a body cavity and the wire is then moved out through the needle. The wire is provided with curved memory characteristics that cause the wire to assume a loop shape which is particularly useful for supporting the umbilical cord. This device is not provided with a fastener means at a terminal end of the wire for closing the loop and the narrow cross-section of the wire can cause trauma to the held organ.

U.S. Pat. No. 4,592,355 to Antebi describes an instrument that is useful for tying live tissue. This instrument comprises a flexible strap that is looped around the body tissue and inserted into a head member. Teeth on the strap engage a pawl in the head to prevent the loop from opening. This strap is particularly useful for ligating hemorrhoidal tissue because once the strap is tightened, it is not intended to be loosened.

The prior art also has described numerous snare devices having narrow width belts or wires that are useful for holding a body organ, cutting tissue and removing malignant growths. Representative of these devices are U.S. Pat. Nos. 480,870; 668,647; 1,461,864; 1,470,914; 2,054,149; 3,181,533; 3,828,790; 5,084,054 and 5,163,942.

What is therefore needed is a grasper device having a strap means housed inside a tube serving as a conduit means for the strap, and wherein the strap is detachable from either the conduit means or a manipulative means housed therein. Such a detachable strap is useful for encircling a body organ, such as a colon or umbilical cord, that is connected to adjoining body tissue at both ends. A terminal end of the strap is provided with an attachment means that is manipulated by a forceps-type device to attach the strap means to close the connection means to close the loop around the body organ. The closed loop and associated grasper device is then useful for holding and manipulating the body organ. The strap can further be provided with memory-curved characteristics that provide the strap defining a partially closed loop upon deployment from the conduit means.

In that respect, the strap needs to be flexible to provide for adjusting the size of the loop, but have relative rigidity in a plane normal to the loop to provide maneuverability for positioning the loop over and around a target body organ and for manipulating the body organ. The strap means should atraumatically grip the body organ or tissue in a manner preventing the tightened loop from slipping on the organ or tissue as the device is used to manipulate the same. The strap also needs to be sealed inside the tube so that gases and fluids present inside the body cavity are prevented from escaping through the tube while the seal provides for strap movement along the tube. A locking means should be readily accessible to the user of the device and serve to lock the movement to maintain the loop size.

These and other aspects of the present invention will become increasingly apparent to those of ordinary skill in the art by reference to the following descriptions and to the drawings.

GENERAL DESCRIPTION OF THE INVENTION

The grasper device according to the present invention comprises a flexible strap that is initially housed inside a tube serving as a conduit means for the device. The tube is moved through the cannula port so that a distal portion of the tube is inside the body cavity and a proximal, handle portion is outside the body. The strap is provided with a distal section having an attachment means preferably comprising a locking aperture provided at a terminal end thereof. Manipulative means operatively associated with the strap is manipulated adjacent to the proximal portion of the tube to deploy the distal strap section from the tube.

A second grasper device, preferably in the form of a laparoscopic forceps-type device, is introduced into the body cavity through a separate cannula port. This device is used to grasp and manipulate the terminal end of the distal strap section to mate the attachment means with a strap connection means provided either on the conduit means or the manipulative means to complete the loop, closed around the body organ. The strap manipulative means is then manipulated to retract the strap into the tube and thereby tighten the loop to hold the body organ. A locking means is provided on the tube to selectively maintain various sizes of the loop. There is also a sealing means in the tube that is provided to seal around either the strap or the manipulative means for the strap to prevent gas and fluids present inside the body cavity from moving through the tube to the proximal end thereof.

The strap section forming the loop is preferably provided with gripping formations such as ridges, studs, serrations, recesses or openings of various shapes and the like on the inner surface thereof or the strap can be provided with scalloped edges. Openings are preferred because they allow moisture trapped under the strap to escape while organ tissue pushes into the openings which function to atraumatically grip the organ tissue as the loop is tightened and then manipulated to move the body organ.

An important feature of the strap is that it is semi-rigid in a first plane aligned along the face of the strap, yet flexible in a second plane normal to the first. This rigidity allows the surgeon to easily maneuver the defined loop. A strap guide mounted on the tube restrains rotational movement of the strap, i.e., rotation of the strap around a longitudinal axis of the strap, and thereby allows the surgeon to manipulate the target organ in a controlled fashion.

The attachable strap provides the grasper device of the present invention as a particularly useful device in laparoscopic procedures for holding and manipulating body organs that are not provided with an open end, but instead are attached to adjoining body tissue at both ends. Such organs include but are not limited to the colon and an umbilical cord within the uterus.

BRIEF DESCRIPTION OF THE DRAWINGS

FIG. 1 is an elevational view of one preferred embodiment of the grasper device 10 of the present invention comprising a flexible strap 14 having a distal section 18 that is closed to define a loop 20 by manipulatively attaching strap 14 to the connection means 54 of guide 40 provided on a tube 12 having a handle 88 for manipulating the grasper device 10.

FIG. 2 is an enlarged, cross-sectional view along line 2—2 of FIG. 1.

FIG. 3 is an enlarged, cross-sectional view along line 3—3 of FIG. 1.

FIG. 4 is an enlarged, cross-sectional view along line 4—4 of FIG. 1.

FIG. 5 is an enlarged, cross-sectional view along line 5—5 of FIG. 1.

FIG. 6 is an enlarged and broken cross-sectional view along line 6—6 of FIG. 2.

FIG. 7 is a fragmentary plan view of the strap 14 comprising the grasper device 10 shown in FIG. 1 and having gripping formations 34.

FIG. 7A is a partial cross-sectional view of strap 14 having beveled openings 34A.

FIG. 7B is a partial cross-section view of strap 14 having recessed openings 34B.

FIG. 12 is an elevational view of a second embodiment of a grasper device 200 of the present invention.

FIG. 13 is an enlarged longitudinal sectional view along line 13—13 of FIG. 12.

FIG. 14 is a cross-sectional view along line 14—14 of FIG. 13.

FIG. 15 is a cross-sectional view along line 15—15 of FIG. 13.

FIG. 16 is an enlarged longitudinal sectional view along line 16—16 of FIG. 13.

FIG. 17 is a cross-sectional view along line 17—17 of FIG. 16.

FIG. 18 is an elevational view of FIG. 17 rotated to a normal position.

FIG. 19 is a cross-sectional view along line 19—19 of FIG. 16.

FIG. 20 is a cross-sectional view along line 20—20 of FIG. 16.

FIG. 21 is an enlarged, fragmentary elevational view showing locking lug 252 of strap guide 236 seated in joggle-shaped channel 258.

FIG. 22 is a partial and broken cross-section view of a third embodiment of a grasper device 400 Of the present invention.

FIG. 23 is a cross-sectional view along line 23—23 of FIG. 22.

FIG. 24 is a cross-sectional view along line 24—24 of FIG. 22.

FIG. 25 is a cross-sectional view along line 25–25 of FIG. 22.

FIG. 26 is a cross-sectional view along line 26—26 of FIG. 22.

FIG. 27 is a cross-sectional view along line 27—27 of FIG. 22.

FIG. 28 is a cross-sectional view along line 28—28 of FIG. 22.

DETAILED DESCRIPTION OF THE INVENTION

Figure 11:
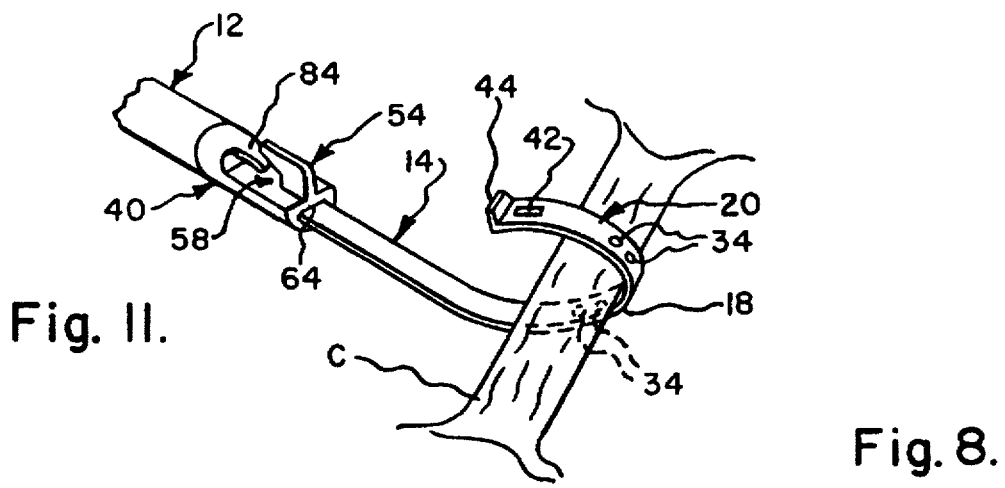
FIG. 11 is a partial perspective view of the grasper device 10 of the present invention showing tube 12 and guide 40 with the distal section 18 of strap 14 cradled around the body organ such as a colon C which is connected to body tissue at each end.

As defined in this application, the word "distal" is used to describe that portion of the device which extends away from the user during operation, and the word "proximal" is used to describe that portion of the device that extends toward the user during operation Further, the terms "upper", "upwardly", "down", "downwardly", "outwardly", "lower", "right" and "left" simply refer to the orientation of FIGS. 1 to 28, and are not intended to be limiting.

Referring now to the drawings, FIGS. 1 to 11 show one preferred embodiment of a grasper device 10 of the present invention. Grasper device 10 includes a conduit means 12 comprising a tube which houses a flexible strap 14 (FIG. 7) having a generally narrow width along its length between a first, proximal section 16 and a second, distal section 18. If desired, the second strap section 18 can be provided with memory characteristics that cause the second section 18 to assume a curved shape defining at least a partially closed loop 20 (FIG. 11) upon deployment of the strap 14 from the tube 12, as will be explained in detail presently.

Loop 20 is useful in laparoscopic surgical procedures for holding and manipulating a body organ and or body tissue contained inside a body cavity such as the abdomen that are not provided with an open end, but instead are, attached to adjoining body tissue at both ends. Examples of this type of body organ include the colon C (FIG. 11) and an umbilical cord within the uterus (not shown). For a description of a laparoscopic grasper device that is particularly useful for holding and manipulating a body organ/body tissue that is open at one end, reference may be made to U.S. Pat. No. 5,417,684 to Jackson et al., and entitled "Laparoscopic Surgical Grasper With a Loop With Gripping Formations", and which is assigned to the assignee of the present invention, the disclosure of which is herein incorporated by reference.

Grasper device 10 is introduced into a body cavity, such as the abdomen, by means of a cannula port (not shown) that is inserted into the abdominal wall by means of a trocar (not shown), as is well known to those skilled in the art. For a more detailed description of such a trocar device and its use, reference may be made to U.S. Pat. No. 4,654,030 to Moll et al; the disclosure of which is hereby incorporated by reference. In that manner, tube 12, which is preferably made of metal or plastic, has a cylindrically shaped sidewall 22 with an inside passage 24 (FIG. 6) that extends along a longitudinal axis A—A of tube 12 between a proximal portion 26 and a distal portion 28 having respective proximal and distal open ends 30 and 32 (FIG. 6). Tube sidewall 22 is sized to fit inside the cannula port for introduction of grasper device 10 into the body cavity with tube 12 serving as a conduit for strap 14.

Strap 14 is made of a suitably flexible plastic material and preferably the plastic material is a polyacetal thermoplastic polymer. Such a material is sold by DuPont under the tradename DELRIN. That way, the first strap portion 16 is useful as a manipulative means to move strap 14 along and through the inside passage 24 to deploy the second strap section 18 out through the distal open end 32 of tubes 12 and to retract the second section 18 inside tube 12 in a manner which will be described in detail presently. While not shown in FIGS. 1 to 11, a separate drive rod can be disposed inside passage 24 and be provided with a distal end attached to strap 14 for manipulating strap 14. Such a drive rod is shown and described in another embodiment of the grasper device 200 shown in FIGS. 12 to 21, and again in still another embodiment of the grasper device 400 shown in FIGS. 22 to 28, both which will be described in detail hereinafter.

Figure 8:
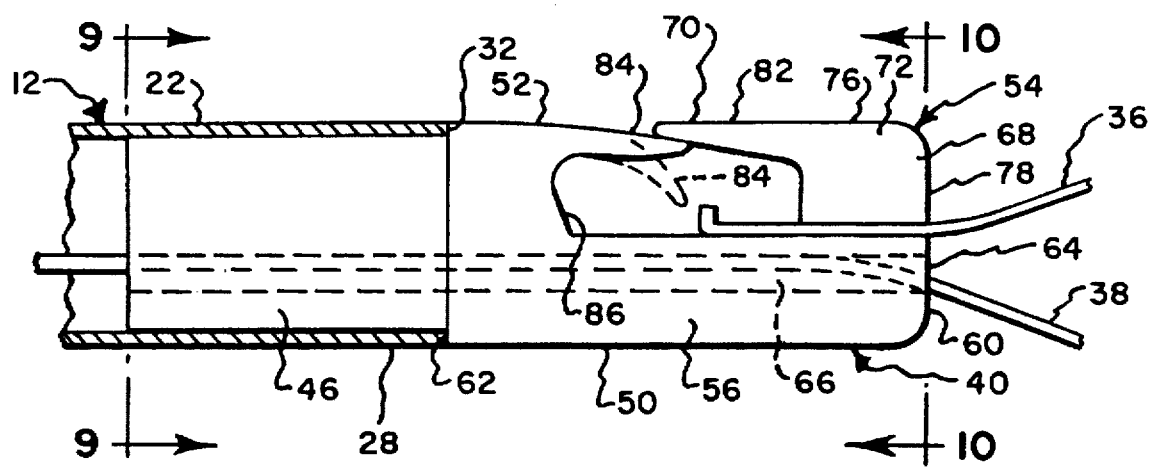
FIG. 8 is a partial cross-sectional view of the grasper device 10 of the present invention showing guide 40 fitted in tube 12 and the distal section 18 of strap 14 attached to the connection means 54 provided on guide 40.

As previously shown in FIG. 7, strap 14 has a continuous inner surface with gripping formations in the form of perforations or openings 34 (FIGS. 7, 7A and 11), preferably having a circular shape, provided at spaced locations or intervals along a holding section of strap 14, the holding section shown extending at least between points 36 and 38 in FIGS. 1 and 8 along the second strap section 18. Although openings 34 are shown having a circular shape with a constant diameter extending completely through the thickness of strap 14, it should be understood that openings 34 need not extend completely through the strap thickness such as recessed opening 34B in FIG. 7B, and they may have a beveled shape, such as openings 34A in FIG. 7A, a polygonal shape or a shape having partially curved and partially straight sides. That way, openings 34 serve as formations to facilitate gripping the colon C or other body organ when loop 20 is positioned and tightened around the body organ, in a manner which will be described in detail presently. If beveled openings 34A are provided on strap 14, preferably the narrow diameter of the bevel faces inwardly, i.e., the narrow diameter of openings 34A face the body organ. Although not shown in the drawings, it is contemplated by the scope of the present invention that the gripping formations can also comprise ridges, studs and serrations provided on the inner surface f strap 14 or that strap 14 can be provided with scalloped edges.

A guide means 40 for the strap means 14 is fitted into the distal open end 32 of tube 12 and serves to hold and direct the movement of strap 14 through tube 12 as the second strap section 18 is extended from and retracted into the tube 12 without allowing strap 14 to rotate, i.e., guide 40 prevents strap 14 from rotating about its longitudinal axis and about the longitudinal axis of the tube 12. This provides the surgeon or attending person with control of the loop 20 so that during a surgical procedure loop 20 is maneuverable around a body organ, such as representative colon C (FIG. 11) to thereby cradle and hold the organ.

As shown in FIG. 7, the second section 18 of strap 14 has an attachment means comprising an attachment aperture 42 proximate a terminal end thereof having an upwardly projecting step 44. Aperture 42 has a rectangular shape aligned along the axis of strap 14. This provides for attaching the second section 18 of strap 14 to a strap connection means provided on the guide means 40, as will be explained in detail presently.

Figures 9, 10:
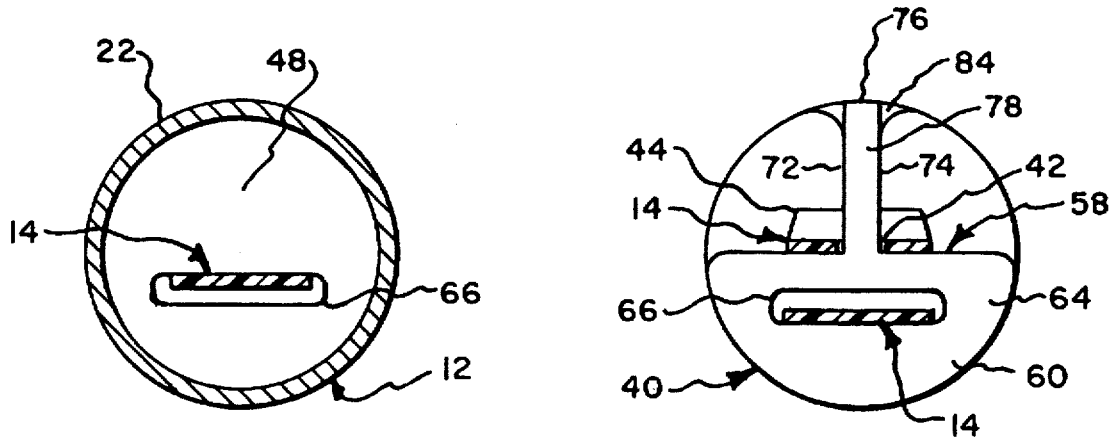
FIG. 9 is a cross-sectional view along line 9—9 of FIG. 8.
FIG. 10 is a cross-sectional view along line 10—10 of FIG. 8.

In particular, guide means 40, as shown in FIGS. 8 to 10, is formed as a body that is preferably made if a metal or a plastic material, and, if plastic, preferably it is an acetal material, such as DELRIN. Guide 40 has a cylindrically shaped insert portion 46 (FIG. 8) having an elongated and narrow opening 48 and a tip portion 50. Tip 50 has a first part 52 adjacent to insert 46 and a second part comprised of upper and lower tip portions 54 and 56. Upper portion 54 provides the connection means for the strap 14 and extends from an upper surface 58 of the lower guide tip portion 56, lower tip 56 further having an outer face 60 thereof. Insert portion 46 has an outer diameter substantially equal to the inner diameter of tube 12 so as to be in a snug-fitting relationship with the inside passage 24 of tube 12 with an annular ledge 62 formed at the junction of insert 46 and the first part 52 of tip 50 abutting against the distal open end 32 of tube 12. To insure that the guide 40 does not inadvertently separate from its snug-fitting relationship with the inside passage 24, the tube 12 is swaged down into the insert portion 46. Further, the guide 40 can be provide as a selectively removably mounted member in the distal open end of the tube 12, as will be explained in detail with respect to another embodiment of the grasper device 200 shown in FIGS. 12 to 21.

As shown in FIG. 10, outer face 60 of guide 40 is provided with an elongated and narrow opening 64 in the shape of a slot with curved or rounded corners that provides an aperture to a longitudinal channel 66 (FIGS. 6 and 8), which extends from outer face 60 along a plane parallel to the axis A—A of grasper device 10 and through the length of the tip 50 and the insert 46. Channel 66 is dimensioned to allow sliding and guiding movement of the strap 14 therealong while preventing the strap 14 from rotating about its longitudinal axis.

As shown in FIGS. 1, 6, 8, 10 and 11, strap connection means 54 extends upwardly from surface 58 of lower tip portion 56 and comprises a rectangular-shaped locking extension 68 provided with a cantilevered clasp member 70. The locking extension 68 and clasp 70 comprising the connection means 54 have opposed planar sidewalls 72 and 74 (FIG. 10) extending perpendicularly from surface 58 to an upper wall 76 joining with front and back walls 78 and 80. Upper wall 76 is essentially coplanar with the sidewall 22 of tube 12 while front wall 78 of locking extension 68 is coplanar with the outer face 60 of guide 40. Back wall 80 is parallel with front wall 78 and extends upwardly from planar surface 58 to a backwardly projecting, angled lower wall 82 of clasp 70 forming a rounded tip where lower wall 82 meets upper wall 74. Clasp 70 and locking extension 68 are sized to mate with attachment aperture 42 provided at the terminal end of the second strap section 18 to complete loop 20, as will be described in detail presently.

As particularly shown in FIGS. 1, 6, 8 and 11, a resilient locking tang 84 extends forwardly from a front wall 86 of the first part 52 of guide tip 50. Tang 84 is a semi-flexible member that is normally in an overlapping relationship with clasp 70, the latter being positioned over and above tang 84. That way, tang 84 serves to lock the terminal end of strap 14 on locking extension 68 after attachment aperture 42 has been moved over clasp 70 and positioned around extension 68, preferably laying on the planar surface 58 of the lower tip portion 56 of guide tip 40 to complete the loop 20, as will be described in detail presently.

In the grasper device 10 illustrated herein, the strap connection preferably is provided on the guide means 40. In a broader sense, however, and in accordance with the scope of the present invention, the strap connection means can be provided at other locations on the distal end of the conduit means 12 and even on a manipulative means for strap 14 comprising an attachment rod disposed in a movable relationship inside tube 12. This latter embodiment will be described with respect to two other embodiments of the present invention shown hereinafter in FIGS. 12 to 21 and 22 to 28 respectively.

As shown in FIGS. 1 and 6, a handle 88, preferably made of a metal or plastic material is mounted on the tube sidewall 22 at the proximal portion 26 of tube 12. Handle 88 has a cylindrically shaped mounting portion 90 and an enlarged proximal portion 92 having an end face 94 (FIG. 4). A first inner opening 96 extends longitudinally along the mounting portion 90 and is sized to receive the proximal portion 26 of tube 12 in a snug-fitting relationship with the proximal open end 30 of the tube 12 abutting an inner annular ledge 98 provided at the proximal extent of opening 96. Annular ledge 98 leads to a second inner opening 100 extending the remaining length of mounting portion 90 to a restricted cross-section portion 102 provided adjacent to the enlarged portion 92. Restriction 102 narrows to a slot-like channel 104 (FIGS. 2 to 4 and 6) that extends longitudinally along the length of enlarged handle portion 92 to the central part of an annular recess 106 (FIGS. 4 and 6) provided in end face 94. A plurality of threaded openings 108 are provided through end face 94 and extend into enlarged handle portion 92 spaced at uniform intervals around the annular recess 106 (FIG. 4).

As shown in FIGS. 1 to 3, 6, and 7, a retainer member 110 having an inner, narrow slot-like oval channel 112 that extends to an annular recess 114 (FIG. 6), is mounted on the end face 94 of handle 88 by a plurality of screws 116 (FIGS. 2 to 4 and 7) fitted through countersink openings 118 in retainer 110 and threadedly received in handle openings 198. Retainer recess 114 and handle recess 106 are aligned and together provide a cavity for mounting a sealing means in the form of a disc-like member 120 (FIGS. 4 to 6) having a slit 122 (FIG. 4) that fits snugly around the perimeter of strap 14. Sealing means 120 serves to seal around strap means 14 to prevent gases and fluids present inside the body cavity from moving through the conduit means 12 to the proximal open end 30 thereof when the distal portion 28 of the conduit means 12 is inserted into the body cavity, the sealing means also allowing movement of the strap means 14 along the conduit means 12. Strap 14 extends through oval channel 112 to locate the first strap section 16 outwardly and upstream of retainer member 110. Strap section 16 has a terminal aperture 124 (FIGS. 6 and 7) that receives a screw 126 which threads into a threaded opening 128 provided in the sidewall of retainer 110 to mount the end of first strap section 16 to the retainer 110. Retainer 110 is also preferably made of a metal or plastic material, and if plastic, preferably it is a polyacetal material, such as DELRIN.

There is also provided a locking means that is accessible from a remote location outside the body cavity to selectively allow and prevent movement of strap 14 along and through the inner passage 24 in the tube 12 to deploy and retract the second strap section 18 from the outer opening 64 in the outer face 60 of guide 40. The locking means is movable to an enabled or engaged position (FIGS. 2, 3 and 6) to prevent movement of strap 14 along the inner passage 24 of conduit means 12 and is movable to a disabled or disengaged position (not shown) to allow such movement of strap 14.

As shown in FIG. 6, the locking means comprises a locking screw 130 having a knurled thumb wheel 132 and a threaded shaft 134 that is received in a second threaded opening 136 provided in retainer 110, opposite terminal screw 126. The axis of the threaded shaft 134 is normal to the plane of oval channel 112 such that when locking screw 130 is threaded into the opening 136 a sufficient distance, as shown for example in FIG. 6, the end of shaft 134 contacts strap 14 and holds strap 14 against a stop means in the form of a surface 138 (FIGS. 3 and 6) of channel 112. This serves to lock strap 14 in place to prevent the first strap section 16 from being manipulated. In that respect, when the locking screw 130 is enabled and contacts strap 14 against surface 138, the first strap section 16 is prevented from being manipulated in a forward direction, as indicated by arrow 140 in FIGS. 1 and 6. This prevents deployment of the second section 18 of strap 14 out through the narrow opening 64 in outer face 60 of guide 40, which deployment enables the second strap section 18 to be manipulated to form loop 20, as will be explained in detail hereinafter. When the locking screw 130 is enabled, the first strap section 16 is also prevented from being manipulated to tighten the loop 20 by retracting strap 14 into the tube 12, as indicated by arrow 142 in FIGS. 1 and 6 once the attachment aperture 42 has been attached to the locking extension 68 of the strap connection means 54 to complete loop 20.

When locking screw 130 is in a disengaged position (not shown), unthreaded from contact with strap 14 and with the distal portion 28 of tube 12 adjacent to a target body organ, the first section 16 of strap 14 is manipulatable in a forward direction as indicated by arrow 140 in FIGS. 1 and 6, to extend the second strap section 18 out through the narrow opening 64 in the outer guide face 40. The strap attachment aperture 42 is positionable on the strap connection means 54 by appropriate manipulation with a laparoscopic forceps-type device, which has been separately introduced into the body cavity device, to mate the attachment 42 with extension 68 and complete loop 20, as will be described in detail presently.

In the case of the second strap section 18 having memory-curved characteristics, movement of this section forms loop 20 in a partially extended relationship around colon C (FIG. 11) due to the memory-curved characteristics. Handle 110 is then manipulated to move the partially formed loop 20 to a desired position axially along the length of the body organ and the terminal strap aperture 42 is attached to strap connection means 54 to complete the loop 20.

With loop 20 secured to extension 68, the proximal portion of strap 16 is movable by hand in a rear rearward direction, as indicated by arrow 142 in FIGS. 1 and 6, to tighten loop 20 around colon C and permit strap openings 34 to grasp and lock onto the body organ. The surgeon is then able to perform the intended surgical procedure by manipulating grasper 10 to move the organ as needed.

In use, the grasper device 10 of the present invention provides for holding and manipulating a body organ inside a body cavity from a remote location outside the cavity during a surgical procedure. In that respect, grasper device 10 is inserted into the body cavity through a cannula port (not shown) so that the distal portion 28 of the tube 12 is inside the body cavity while the proximal tube portion 26 and handle 88 are outside the body cavity at the remote location. To facilitate movement of grasper device 10 through the cannula port, strap 14 is preferably housed inside tube 12 with the upwardly extending strap 44 at the terminal end of the second section 18 abutted against the outer guide face 60.

Typically, in a laparoscopic surgical procedure, carbon dioxide is pumped into the abdomen to separate the body organs contained therein from the abdominal sidewall. Thus, sealing means 120 serves to contain this carbon dioxide gas and other body fluids to prevent them from moving through inner passage 24 in tube 12 to the proximal open end 30 thereof.

With the distal tube portion 28 inside the body cavity and the locking means 130 disengaged, the first section 16 of strap 14, which extends through the proximal open end 30 of tube 12 is manipulated from the remote location to move strap 14 in a forward direction, as indicated by arrow 140 in FIGS. 1 and 6, to push the strap 14 out through the guide opening 64 to extend the second strap section 18 out through the outer guide face 60. Channel 66 in guide 40 serves to direct this sliding movement without allowing strap 14 to rotate about its longitudinal axis. In other words, there is no rotation of strap 14 relative to the longitudinal axis of tube 12. This provides the surgeon with control of the second strap section 18. In the case of the second strap section 18 have memory-curved characteristics, by manipulating handle 110 and the first section 16 of strap 14, the surgeon is able to deploy the second strap section 18 to begin forming loop 20 and position the partially defined loop 20 around a target body organ. Since strap 14 is relatively rigid in a plane normal its width, loop 20 can be then moved axially along the body organ to a desired position.

Whether or not the second strap section 18 is provided with memory-curved characteristics, in order to complete the loop 20 around colon C, it is necessary for the surgeon or other attending person to grasp ahold of the terminal end of strap 14 adjacent to attachment aperture 42 by means of a second manipulation means preferably comprising a pair of laparoscopic forceps (not shown). These forceps are manipulated to move strap 14 toward the strap connection means 54. Aperture 42 is sized to fit over and around the locking extension 68 so that once rectangular opening 42 is moved over clasp 70, the distal section 18 of strap 14 is able to be pulled away from guide 40, as shown by arrow 140 in FIGS. 1 and 6, to slide the attachment aperture 42 along clasp 70 until opening 42 is positioned at the junction of clasp 70 and extension 68. At this point, the aperture 42 is able to be moved completely over extension 68 and positioned against the planar surface 58, as shown in FIGS. 1, 6, 8 and 12. Locking tang 84 has a semi-rigid characteristic that enables it to flex in a downwardly direction, as shown in dotted lines in FIG. 8, to enable the aperture 42 to slide over clasp 70. Once aperture 42 is clear of tang 84, tang 84 returns to its original position overlapped by clasp 70. This serves to lock the strap 14 around the connection means 54 and around the target body organ, such as colon C.

The first section 16 of strap 14 is then pulled in a rearward direction, as indicated by arrow 142 in FIGS. 1 and 6, to tighten loop around the body organ for holding the body organ. As this happens, moisture trapped under strap 14 escapes into the formations, such as openings 34 (FIG. 7) and organ tissue pushes up into the openings 34, which in conjunction with the continuous inner surface of the strap 14 serve to atraumatically grip the colon C tissue.

With the body organ held in loop 20, the surgeon can rotate locking screw 130 in a first direction to thread shaft 134 into threaded opening 136 in the retainer 110 so that the end of shaft 134 contacts the strap 14 (FIGS. 2, 3 and 6) and holds it against the stop means 138 to thereby hold the loop 20 in position around the body organ. The surgeon is then able to manipulate the handle 88 to move the body organ as needed during the surgical procedure.

At such time as grasper device 10 is no longer needed to manipulate the body organ, the locking screw 130 is rotated in a second direction to unthread shaft 134 from opening 136 to release the end of shaft 134 from strap 16 so that the first section 16 of strap 14 can be first pushed forward, as indicated by arrow 140 of FIG. 6, to open loop 20. A scissors instrument (not shown), introduced into the body cavity through a separate cannula port (not shown), is used to sever the strap 14 at a point adjacent to guide 40 to free strap 14 from around the body organ. Part of the strap 14 having the attachment aperture 42 will remain secured to the strap connection means 54 while the severed end will extend freely from opening 64 in end face 60 of lower guide tip portion 56. Handle 88 can be manipulated to remove the severed portion of strap 14 from around the body organ, and then the strap 14 can be pulled rearwardly, in the direction of arrow 142 in FIG. 6, to retract the strap 14 into guide 40. The grasping device 10 is then pulled out of the body cavity through the cannula port, and the surgical procedure is completed as required.

At such time as the use of the grasper device 10 is no longer needed in the surgical procedure, the grasper device 10 is preferably disposed of. However, it will be apparent to those skilled in the art that reusable designs for the grasper device are contemplated within the scope and breadth of the present invention.

FIGS. 12 to 21 show another embodiment of a grasper device 200 of the present invention. This grasper device 200 comprises a tube 202 having a proximal portion 204 and a distal portion 206 (FIG. 13) providing an inner opening or lumen extending between respective proximal and distal open ends 208 and 210 and along a longitudinal axis B—B thereof. The proximal tube portion 204 is mounted inside of a first, inner handle opening 212 that extends longitudinally a portion of the length into a cylindrically shaped handle 214 to an inner annular ledge 216 thereof. A drive means in the form of drive rod 218 is located inside tube 202 and handle 214.

A flexible strap 220, similar to strap 14 (FIGS. 1 to 11) is removably attached to the distal portion 222 of drive rod 218. Although not shown in FIGS. 12 to 21, strap 220 has a continuous inner surface provided with gripping formations in the form of perforations or openings similar to openings 34 in strap 14 (FIGS. 7, 7A, 7B and 11). The gripping formations in strap 220 need not extend completely through the strap thickness, and they serve as formations to facilitate gripping the body organ at such time as a loop (not shown in FIGS. 12 to 21) is positioned and tightened around the body organ.

As shown in FIGS. 14 and 15, drive rod 218 is, for the majority of its length, a cylindrically shaped member having a circular cross-section dimensioned and disposed to be received in the inner opening of tube 202 and extending to a rectangular shaped distal portion 222 (FIG. 19). A pair of cylindrically shaped connecting posts 224 and 226 having rounded ends extend from the respective major planar surfaces 224A and 226A of the distal portion 222 and diagonally offset with respect to each other. In the longitudinal view shown in FIG. 16, post 224 depends downwardly from surface 224A adjacent to the cylindrical portion of drive rod 218 while post 226 extends upwardly from surface 226A proximate the curved terminal end 228 (FIG. 17) of drive rod 218.

In this embodiment of the grasper device 200 of the present invention, the first section 230 and second section 232 of strap 220 are each provided with respective attachment eyelet openings 230A and 232A that are sized to mate with and thereby receive the respective posts 224 and 226. Thus, the eyelet openings 230A and 232A provide strap attachment means that are removably mated with the connecting posts 224 and 226 to attach the strap 220 to drive rod 218 and provide a loop 234 (FIG. 13) for encircling and manipulating a body organ, preferably a body organ connected at both of its ends to associated tissue such as the representative colon C (FIG. 11). The manipulation of strap 220 to form the loop 234 for encircling the body organ will be explained in detail hereinafter.

The grasper device 200 of the present embodiment is also useful for manipulating a body organ that is connected at only one of its ends such as a spleen and the like. In that case, the second strap section 232 does not need to be removed from the post 226 and the drive rod 218 is manipulated to adjust the loop 234 size to a sufficient size to move the loop 234 over the "free end" of the body organ and to tighten the loop around the body organ, as was previously described with respect to the grasper device 10 shown in FIGS. 1 and 11.

As shown in FIGS. 12, 13 and 16 to 18, a guide means 236 is provided at the distal open end 210 of tube 202. Guide 236 serves to hold and direct sliding movement of strap 220 through tube 202 to thereby provide the loop 234 while preventing the strap 220 from rotating about its longitudinal axis, i.e., the length of strap 220 relative to the longitudinal axis B—B of tube 202 as loop 234 is tightened on the body organ to manipulate the organ. In particular, guide means 236 is a cylindrically shaped body that is preferably made of a metal or plastic material, and if plastic, preferably it is an acetal material. Guide means 236 has an annular outer surface extending between an insert portion 238 having an inner face 240 (FIGS. 16 to 19) and a tip portion 242 having an outer face 244 (FIGS. 14 and 16 to 18). Insert portion 238 has an outer diameter substantially equal to the inner diameter of tube 202 so as to be in a snug-fitting relationship with the inner surface thereof with an annular ledge 246 abutting against the distal open end 210 of tube 202. Ledge 246 is defined by the junction between insert portion 238 and tip 242.

As shown in FIGS. 19 and 20, guide 236 is removably mounted in the distal open end 210 of tube 202 by means of locking lugs received in corresponding joggle slots. Three locking lugs 248, 250 and 252 are provided at unequal annular positions on the inner surface 202A of the tube 202, and along a plane normal to the longitudinal axis B—B of tube 202 and spaced inwardly from the distal open end 210 thereof. With respect to the orientation of FIG. 20, lug 248 is positioned at about twelve o'clock, lug 250 is positioned at about five o'clock and lug 252 is positioned at about seven o'clock. The locking lugs 248, 250 and 252 are received in correspondingly positioned locking joggle slots 254, 256 and 258 provided in guide 236, slot 258 being shown in detail in FIG. 21. Joggle slot 258 is representative and comprises a first channel 260 having a rectangularly shaped cross-section extending along a portion of the sidewall of insert portion 238 from the inner face 240 to a second channel 262. Second channel 262 comprises a normal sidewall 264 extending at a right angle from a first sidewall 266 of channel 260 and an angled sidewall 268 extending obliquely from a second sidewall 270 of channel 260. A pivotable locking tang 272 is provided at the junction of the second sidewall 270 of channel 260 and the angled sidewall 268 of channel 262, and extends through the second channel 262 and into a third rectangularly shaped channel 274 which is parallel to the first channel 260 and generally normal to second channel 262.

It is also contemplated by the scope of the present invention that guide 236 can be pressed, fitted or swaged into the distal open end 210 of tube 202 in a similar manner as guide 40 is fitted into the distal open end 32 of tube 12 (FIGS. 1, 6 and 8 to 11).

As shown in FIGS. 16 to 20, guide 236 is further provided with a through opening 276 having a generally inverted T-shaped cross-section with respect to the orientation of FIGS. 19 and 20. In that respect, opening 276 is formed from a large rectangular section 278 and an inverted channel shaped section 280 extending to and joining with the rectangular section 278 at about the midpoint of its width. The rectangular portion 278 has a sufficient width and height to provide fox receiving the distal portion 222 of drive rod 218 and for allowing sliding and guiding movement of the first and second sections 230 and 232 of the strap 220 therealong. Thus, strap 220 is doubled back upon itself with the first and second strap sections 230 and 232 moved through the rectangular section 278 of guide opening 276 and with the channel shaped section 280 allowing for movement of post 226 therethrough while post 224 is prevented from movement past guide 236 by the inner face 240.

As shown in FIG. 18, the distance separating posts 224 and 226 along the length of the distal portion 222 of the drive rod 218 with respect to the length of the guide 236 between faces 240 and 244 is such that appropriate forward movement of drive rod 218 to the position shown in this figure exposes the end of strap 220 and eyelet 232A received on post 226. This provides access to the second strap section 232 for releasing and re-connecting strap 220 to drive rod 218 by appropriate manipulation of strap 220 with respect to post 226 to form loop 234 (FIG. 12) while the first strap section 230 remains confined inside tube 202 by means of eyelet 230A received on post 240 and locked therein by the inner face 240 of guide 236 provided at the distal open end 210 of tube 202.

As previously described, handle 214 is cylindrical in shape having the first opening 212 receiving tube 202 in a snug-fitting relationship and with tube 202 abutting the annular ledge 216, which meets a second slightly smaller diameter inner handle opening 282 formed by inner annular surface 284 (FIGS. 12 to 15). Annular surface 284 extends the remaining length of handle 214 with drive rod 218 movably housed inside the second handle opening 282 and tube 202. As shown in FIGS. 12 and 13, handle 214 is provided with a pair of diametrically opposed axially extending slots 286 and 288 that begin at a point spaced from the proximal open end 290 of handle 214 and extend to a position adjacent to a seal means 292 mounted in an inner annular recess 294 in handle 214.

Seal 292 is preferably made of an elastomeric material having the shape of an O-ring. Seal 292 is mounted in recess 294 before tube 202 is mounted in handle opening 212 by first folding seal 292 upon itself and moving it along the first handle opening 212 and then along the inner handle opening 282 until seal 292 is aligned with annular recess 294. Seal 292 is then unfolded and pressed into recess 294, and tube 202 is snug-fitted into opening 212. When drive rod 218 is positioned inside handle 214 and tube 202, seal 292 fits around the periphery of rod 218 to prevent gases and fluids present inside the body cavity from moving through tube 202 and handle 214 to handle slots 286 and 288. The sealing means 292 allows axial movement of drive rod 218 therethrough and hence along handle 214. As an alternative sealing means embodiment, drive rod 218 is sized to be in a closely spaced sliding relationship with the inner annular surface 282 of handle 214 (FIG. 13), to thereby prevent gases and fluids present inside the body cavity from moving through handle 214 to the slots 286 and 288.

A cylindrically shaped collar 296 having a pin bore 298 (FIG. 14) and an inner annular recess 300 aligned axially with bore 298 is mounted on handle 214 in an axially sliding relationship. Collar 296 is further provided with a threaded opening 302 (FIG. 15) that is offset axially from pin bore 298 and annular recess 300, and which opening 302 receives a locking screw 304 having a knurled thumb wheel 306 and a threaded shaft 308, similar to locking screw 140 (FIGS. 1 to 3 and 6). The threaded shaft 308 of screw 304 is threadedly received in opening 302 and has a diameter that is larger than the width of slots 286 and 288. Collar 296 is connected to drive rod 218 by a connection means comprising a pin 310 that is driven through the collar pin bore 298 and mounted in an opening 312 in the proximal portion of drive rod 218 so that the opposed end portions of pin 310 extend past opening 312 and through the opposed handle slots 286 and 288, and are received in the annular recess 300 in collar 296. That way, pin 310 connects drive rod 218 to collar 296 which is axially slidable along handle slots 286 and 288 while annular recess 300 in collar 296 provides for 360° of rotation of collar 296 around handle 214.

The rotatable collar 296 enables locking screw 304 to be positioned at an infinite number of annular positions about the longitudinal axis of device 200 to enable the surgeon to find a comfortable position at which to hold and manipulate a body organ. Thus, screw 304 provides a locking means when it is threaded into opening 302 by turning thumb wheel 306 in a first direction to contact handle 214 so that collar 296 is prevented from being moved axially along handle 214. Turning locking screw 306 in a second, opposite direction moves locking screw 306 to a position, spaced from handle 214. This disables the locking means and enables the collar 296 to be both rotated annularly around handle 214 to change the annular position of the locking means and to be moved axially along handle slots 286 and 288 to deploy the second section 232 of the strap 220 and to adjust the size of the loop 234, as will be described in detail presently.

Thus, the distal end 206 of the grasper device 200 is initially inserted into the body cavity with both the first and second strap sections 230 and 232 connected to the distal portion 222 of the drive rod 218 and forming loop 234. With locking screw 306 in a disengaged position (not shown), unthreaded from contact with handle 214, collar 296 is manipulatable from a remote location outside the body cavity to slide collar 296 in a forward direction along the handle slots 286 and 288, as indicated by arrow 314 in FIGS. 12 and 13. This forward motion provides for moving drive rod 218 along within the handle 214 and tube 202 to thereby cause the post 226 and the distal portion 222 of drive rod 218 to move through the respective channel shaped section 280 and rectangular section 278 of the guide opening 276 to deploy the second section 232 of strap 220.

As previously discussed, post 224 and the first strap section 230 are prevented from moving out, through the distal open end 210 of tube 202 by the inner face 240 of guide 236. Once deployed (FIG. 18), a separate grasper device (not shown) such as a forceps-type device previously introduced into the body cavity through a separate cannula port, is manipulated to grasp ahold of the second strap section 232 to slide the eyelet 232A off of the post 226 and thereby open loop 234. The grasper device 200 is further manipulated from the handle 214 to maneuver the second strap section 232 under and around the body organ such as an organ having both of its ends connected to adjacent body tissue as exemplified by colon C (FIG. 11), and then to again mate eyelet 232A with post 226 to complete loop 234 encircling the body organ.

With loop 234 in place, collar 296 is moved in a rearward direction, indicted by arrow 316 in FIGS. 12 and 13, to move drive rod 218 along within tube 202 and handle 214 to tighten loop 234 and thereby grasp and hold the body organ. As this happens, moisture trapped under strap 220 escapes into the gripping formations (not shown), as previously described, and the organ tissue pushes up into the formations, which in conjunction with the continuous inner strap surface serve to atraumatically grip the body tissue.

During the foregoing, strap 220 and loop 234 are prevented from rotating about the longitudinal axis of strap 220 by guide means 236 as previously described in detail. Collar 296 is freely rotatable about the annular extent of handle 214 to position the locking means at a comfortable and easily manipulatable position for the surgeon. The surgeon is then able to thread the locking screw 306 into contact with handle 214 (FIG. 15) to lock the tightened loop 234 around the body organ and perform the intended surgical procedure by manipulating the organ as needed.

When grasper device 200 is no longer needed to manipulate the body organ, locking screw 306 is unthreaded from contact with handle 214 (not shown) so that collar 296 is once again movable in a forward direction, as indicated by arrow 314 in FIGS. 12 and 13, to move drive rod 218 forwardly to enlarge the size of loop 234. The previously mentioned forceps grasper device (not shown) is again manipulated to disconnect the second section 232 of strap 220 from the distal portion of the drive rod 218 by removing eyelet 232 from post 226 to open the loop 234 from around the body organ. Collar 296 is now moved in a rearward direction, as indicated by arrow 316 in FIGS. 12 and 13, to a fully retracted position adjacent to the proximal open end 290 of handle 214 to retract the strap 220 into guide 236 and tube 202 before grasper device 200 is removed from the body cavity by moving it out through its cannula port (not shown).

Alternatively, the strap 220 is loosened from around the body organ and a separate cutting device (not shown) is manipulated to sever the strap 220 and thereby open the loop 234 from around the body organ. Again, the collar 296 is now moved in a rearward direction to retract the strap 220 into guide 236 and tube 202 before the grasper device 200 is removed from the body cavity.

To assemble the guide 236 to the distal open end 210 of tube 202, the first strap section 230 is first moved through the guide opening 276 and with drive rod 218 housed inside tube 202, eyelet opening 230A is moved over post 224. Similarly, the second strap section 232 is moved through the guide opening 276 and eyelet opening 232A is moved over post 226. The strap 220 is now attached to the drive rod 218 with the guide 236 intermediate the thusly formed loop 234 and the first and second strap sections 230 and 232 attached to the distal drive rod portion 222. Guide 236 is then positioned adjacent the distal open end 210 of tube 202 with the locking lugs 248, 250 and 252 aligned with the corresponding joggle slots 254, 256 and 258. Both the locking lugs and slots are spaced at irregular annular positions around the inner surface 202A of tube 202 and this provides only one relative rotational position for mating guide 236 to tube 202, which will be described herein with respect to representative locking lug 252 and slot 258, as shown in, FIG. 21.

Insert portion 238 is moved into tube 202 with the locking lug 252 passing along the first channel 260 of slot 258 until lug 252 contacts the normal sidewall 264 of second channel 262. Guide 236 is then rotated in a clockwise direction, indicated by arrow 318 in FIG. 21, a sufficient distance to move the lug 252 along the second channel 262 to a position aligned with the third channel 274. As this movement occurs, locking tang 272 pivots towards the angled sidewall 268 of second channel 262, as indicated by arrow 320, to allow free movement of lug 252 to a position aligned with the third channel 274. Guide 236 is then moved further into tube 202 until locking lug 252 abuts against the end wall of the third channel 274. In the course of this movement, locking tang 272 moves in a direction opposite arrow 320 to its original position to thereby lock guide 236 securely inside tube 202. Locking lugs 248 and 250 and their associated locking slots 254 and 256 function in a similar manner when guide 236 is mounted in the distal open end 210 of tube 202, as just described.

As is the case with the grasper device 10 described with respect to FIGS. 1 to 11, this grasper device 200 is preferably disposed of after a surgical procedure. However, it is contemplated by the scope of the present invention that those skilled in the art will understand that parts of the grasper device 200 can also be reusable.

FIGS. 22 to 28 show still another embodiment of a grasper device 400 according to the present invention. As particularly shown in FIG. 22, grasper device 400 comprises a main tube 402, and a secondary tube 404 having a lesser diameter and a somewhat shorter length than the main tube 402. Tube 402 has proximal and distal portions 406 and 408 with an inner opening or lumen extending between respective proximal and distal open ends 410 and 412 and along and around a longitudinal axis thereof. Thus, main tube 402 serves as a conduit means or a strap 414 while the secondary tube 404 serves to confine the movement of an attachment rod 416 along and through a guide means 418 mounted inside the distal open end 410 of the main tube 402. The proximal portion 406 of tube 402 is in turn mounted inside a first handle opening 420 extending longitudinally part way into the length of a cylindrically shaped handle 422 to an inner annular ledge 424 thereof.

The flexible strap 414 is similar to strap 14 (FIGS. 1 to 11) and strap 220 (FIGS. 12 to 21) and is disposed inside tube 402 and handle 422. Strap 414 has a generally narrow width along its length between a first, proximal section 426 and a second, distal section 428. Although not shown in FIG. 22, strap 414 has a continuous inner surface provided with gripping formations in the form of perforations or openings similar to openings 34 in strap 14 (FIGS. 7, 7A, 7B and 11). The gripping formations in strap 414 need not extend completely through the strap thickness, and they serve as formations to facilitate gripping the body organ at such time as loop (not shown in FIGS. 22 to 28) is positioned and tightened around the body organ.

The first strap section 426 is useful as a manipulative means to move the strap 414 along and through the inside passage of the main tube 402 to adjust the length of the second strap section 428 extending out beyond the distal open end thereof, and then to adjust the size of the thusly formed loop after an attachment means (not shown) provided at the distal end of the strap 414 is connected to the hooked end 430 of the attachment rod 416 serving as a strap connection means. Additionally, the attachment rod 416 serves as a drive rod means for the attached strap.

The manipulative and adjusting functions of the first strap section 428 are similar to those provided by the first section 16 of strap 14, as previously discussed in detail with respect to grasper device 10. Further, the attachment means is preferably similar to opening 232A provided at the distal end of strap 220 of the grasper device 200. Still further, the second strap section 428 can be provided with memory curved characteristics, if desired, that cause this strap section to assume a curved shape defining at least a partially closed loop upon deployment from the tube 402, as previously discussed with respect to straps 14 and 220 of respective grasper devices 10 and 200.

As shown in FIG. 22, guide 418 is a cylindrically shaped body having an annular outer surface extending between a tip portion 432 having an outer face 434 and an insert portion 436 having an inner face 438. Insert portion 436 has an outer diameter substantially equal to the inner diameter of the main tube 402 so as to be snug-fitted therein with an annular ledge 440 abutting against the distal open end 412 thereof and with the inner face 438 abutting against the distal end of the secondary tube 404. Ledge 440 is defined by the junction between tip portion 432 and insert portion 436.

As shown in FIGS. 26 and 27, the lower half of guide 418 is provided with an elongated and narrow longitudinal channel 442 having curved or rounded corners. Lower guide channel 442 extends from the outer guide face 434 and through the length of tip and insert portions 432 and 436 to terminate in a flared structure at the inner guide face 438. Lower guide channel 442 serves to hold and direct movement of strap 414 through the main tube 402 while preventing the strap 414 from rotating about its longitudinal axis, i.e., the length of strap 414 relative to the longitudinal axis of tube 402 as the strap 414 is deployed out of and retracted into the tube 402.

Guide 418 is further provided with an upper channel 444 formed by a semi-circular shaped opening 446 beginning at the outer guide face 434 that tapers to an inverted T-shaped opening 448 extending through the insert portion 436 to the inner face 438. Upper guide channel 444 is further provided with an integral U-shaped channel 450 extending between the opposed outer and inner guide faces 434 and 438 in communication with the semi-circular and inverted T-shaped openings 446 and 448. As particularly shown in FIGS. 26 and 27, the U-shaped guide channel 450 in conjunction with the opposed horizontal portion of the inverted T-shaped opening 448 serve to cradle the hooked end 430 of the attachment rod 416 as this end is moved along and out of the guide 414 to provide access to the connector means for the strap. At such time as the strap 414 is attached to the post of the hooked end 430, the opposed lateral portions of the inverted T-shaped opening provide for receiving and confining the width of the strap 414 moved into the guide 418.

As shown in FIG. 22, the attachments rod 416 is generally a cylindrically shaped member having a circular cross-section dimensioned and disposed to be received in the inner opening of the secondary tube 404 and extending between the hooked end 430 serving as the strap connection means and a proximal manipulator end having a T-shaped manipulator 452 connected thereto. Attachment rod 416 further includes a biasing section 454 intermediate its ends that serves to bias a cross-member 456 (FIGS. 22 and 23) attached to the proximal end of attachment rod 416, for a purpose which will be described in detail hereinafter.

As further shown in FIGS. 22 to 25, the inner handle opening 420 extends part of the way through the length of handle 422 to the annular ledge 424 and opening 420 is in communication with a strap passage 458 and an attachment rod passage 460. The strap passage 458 is an elongated and narrow longitudinal passage having curved or rounded corners, as shown in cross-section in FIGS. 23 to 25. Thus, strap passage 458 is dimensional and disposed to receive the strap 414 and to hold and direct movement of strap 414 through the main tube 402 in conjunction with the lower guide channel 442 while preventing the strap 414 from rotating about its longitudinal axis as the strap 414 is deployed out of and retracted into the tube 402.

The attachment rod passage 460 extends part way along the longitudinal extent of handle 422 and for the majority of its length has a generally square cross-section. A channel-shaped opening 462 communicates with the attachment rod passage 460 for a portion of the latters length and provides for movement of the T-shaped attachment rod manipulator 452. Attachment rod passage 460 is further provided with first and second lateral channels 464 and 466 that receive the cross-member 456 attached to the proximal end of the attachment rod 416. That way, in the retracted position (FIG. 22) the hooked end 430 of the attachment rod 416 is received in the upper guide channel opening 444 and the cross-member 456 is biased seated in the first lateral channel 464 in handle 422.

To deploy the hooked end 430 of the attachment rod 416 comprising the connection means, the user first presses in a downwardly direction on the T-shaped manipulator 452, as indicated by arrow 468 in FIG. 22. Once the cross-member 456 is clear of the first lateral channel 464, the T-shaped manipulator 456 is movable in a forwardly direction along the attachment rod passage 460 as indicated by arrow 470 and towards the distal portion 408 of tube 402 to thereby move the hooked end 430 of the attachment rod 416 out through the upper guide channel 444. The extent of such movement of the attachment rod 416 is limited by the length of the channel opening 462 such that when the T-shaped manipulator 452 is in its forwardly most position (not shown), the cross-member 456 is receivable in the second lateral channel 466 and the hooked end 430 of the attachment rod 416 is fully deployed from the upper guide channel 444. At such time as T-shaped manipulator 452 is released, the biasing section 454 of the attachment rod 416 causes the cross-member 456 to register in the second lateral channel 466 to lock the attachment rod 416 in this position.

As is readily apparent to those skilled in the art, the hooked end 430 of the attachment rod 416 is retracted back into the guide 418 by again pressing on the T-shaped manipulator 452 in a downwardly direction to release the cross-member 456 from the second lateral channel 466. The T-shaped manipulator 456 and associated attachment rod 416 are then movable in a rearwardly direction along the attachment rod passage 460 and towards the proximal end of handle 422 in a direction opposite arrow 470 until the cross-member 456 is again aligned with the first lateral channel 464. The attachment rod 416 is secured in the retracted position shown in FIG. 22 by the action of the biasing section 454 registering the cross-member 456 in the first lateral channel 464 after the T-shaped manipulator 452 is released.

It should further be apparent to those skilled in the art that while not shown in FIGS. 22 to 28, grasper device 400 of the present invention is preferably provided with a seal means that fits around the perimeter of the strap 414 in a similar manner as seal 130 fits snugly around the perimeter of strap 414 in the grasper device 10 shown in FIGS. 1 to 11 to prevent gases and fluids present inside of a body cavity from moving through the tube 402 and the handle 422 when the distal portion 408 is inserted into the body cavity. Also, grasper device 400 is preferably provided with a second seal means (not shown) that fits around the periphery of the attachment rod 414 to prevent gases and fluids from moving through the tube 402 and handle 422 in a similar manner as seal 292 described with respect to the grasper device 200 shown in FIGS. 12 to 21. Furthermore, a locking means (not shown) is preferably provided on handle 422 to selectively prevent and enable movement of strap 414 along and through the inner opening in tube 402 and the handle passage 458. Such a locking means is shown and described in FIGS. 1 to 11 with respect to the grasper device 10 of the present invention.

In use, the distal end 408 of the grasper device 400 is inserted into the body cavity with the attachment means (not shown) provided at the distal end of the second strap section 428 is connected to the connection means provided by the hooked end 430 of the attachment rod 416 retracted into the upper guide channel 444. FIG. 22 shows the hooked end 430 in the retracted position, but does not show the second strap section 428 connected thereto. With the strap locking means (not shown) disengaged from contact with the strap 414 the strap connection means is then deployed to both move this member out through the guide 444 and to move the second strap section 414 out through the guide 444, as indicated by arrow 470. As previously discussed, this is done by first pressing in a downwardly direction on the T-shaped manipulator 452, as indicated of arrow 468 in FIG. 22. Once the cross-member 456 is clear of the first lateral channel 464, the T-shaped manipulator 456 is moved in a forwardly direction along the attachment rod passage 460, as indicated by arrow 470, to thereby move the hooked end 430 of the attachment rod 416 out through the upper guide channel 444 and past the outer face 434.

Once the strap 414 and hooked end 430 are deployed, a separate grasper device (not shown) such as a laparoscopic forceps-type device previously introduced into the body cavity through a separate cannula port, is manipulated to grasp ahold of the second strap section 428. The forceps-type grasper is manipulated to maneuver the second strap section 428 off of the hooked end 430 and under and around the body organ, such as an organ having both of its ends connected to adjacent body tissue as exemplified by colon C (FIG. 11). The forceps grasper device is then manipulated to reconnect the attachment means to the connection means provided by the hooked end 430 of the attachment rod 416 to complete the loop (not shown) encircling the body organ.

With the loop in place, the hooked end 430 of the attachment rod 416 is moved in a rearward direction, opposite that indicated by arrow 470 in FIG. 22. The hooked end 430 is retracted into guide 418 by pressing on the T-shaped manipulator 452 in a downwardly direction, as indicated by arrow 468, to release the cross-member 456 from registry with the second lateral channel 466. The T-shaped manipulator 456 and associated attachment rod 416 are then moved in a rearwardly direction until cross-member 456 is aligned with the first lateral channel 464. The T-shaped manipulator 456 is released and the biasing section 454 moves cross-member 456 into registry with channel 464 to lock the hooked end 430 in the retracted position. During a surgical procedure, this is desirable to secure the second strap section 428 in the guide 418 and to prevent the hooked end 430 from interfering with the procedure. The surgeon is now able to manipulate the body organ as needed Next, the first strap section 426 is manipulated in the rearwardly direction to tighten the loop and thereby grasp and hold the body organ. As this happens, moisture trapped under strap 414 escapes into the gripping formations (not shown), as previously described, and the organ tissue pushes up into the formations, which in conjunction with the continuous inner strap surface serve to atraumatically grip the body tissue. The strap locking means (not shown) is then enabled to lock the strap 414 in the tightened position.

When the grasper device 400 is no longer needed to manipulate the body organ, the strap lock means is disabled and the first strap section 426 is once again moved in a forward direction, as indicated by arrow 470, to enlarge the size of the loop. The T-shaped manipulator 452 is also manipulated to deploy the hooked end 430 of the attachment rod 416. The previously mentioned forceps grasper device is again manipulated to disconnect the second strap section 428 from the hooked end 430 of the attachment rod 416 to open the loop from around the body organ. Next, the first strap section 426 and the T-shaped manipulator 452 are appropriately manipulated to retract the respective strap 414 and hooked end 430 back into the guide 418 before the grasper device 400 is removed from the body cavity by moving it out through its cannula port (not shown).

Alternatively, the strap 414 is loosened from around the body organ and a separate cutting device (not shown) is manipulated to sever the strap 414 and thereby open the loop from around the body organ. Again, the first strap section 426 and the T-shaped manipulator 452 are manipulated to move the respective strap 414 and hooked end 430 into the retracted position before the grasper device 400 is removed from the body cavity.

As with the previously described grasper devices 10 and 200, the grasper device 400 can be either disposable or parts thereof can be reused after appropriate sterilization.

It is appreciated that various modifications to the inventive concepts may be apparent to those skilled in the art without departing from the spirit and scope of the present invention.

What is claimed is:

1. A medical device that is insertable into a body cavity during a surgical procedure to hold and manipulate a body organ from a remote location outside the cavity, which comprises:

a) elongated conduit means having a surrounding sidewall providing an inside passage and extending to proximal and distal portions having respective spaced apart open ends, wherein the proximal portion of the conduit means provides a handle means for inserting the distal portion into the body cavity and for manipulating the distal portion from the remote location;

b) flexible strap means having a width and a thickness so as to be in a movable relationship in the inside passage of the conduit means, and at least a portion of the strap means is extendable out through the distal open end of the conduit means wherein the strap means has a first section and a second section; and c) manipulative means operatively associated with the strap means and manipulatable from the remote location to move the strap means along the inside passage of the conduit means to extend at least the second section of the strap means out through the distal open end of the conduit means, wherein the strap means is provided with an attachment means which upon extension of the second section of the strap means out through the distal open end of the conduit means is either initially in an unattached state and attachable to a strap connection means provided by the medical device or first detachable from the strap connection means and then reattachable thereto such that the attachment means is removably mated to the strap connection means with either the attachment means surrounding the strap connection means or strap connection means surrounding the attachment means to thereby define a loop encircling the body organ and having relative rigidity in a plane normal to the loop, and wherein upon formation of the loop, the handle means and the manipulative means are manipulatable from the remote location to position and tighten the defined loop around the body organ.

2. The medical device of claim 1 wherein the second section of the strap means is provided with memory-curved characteristics that cause the second section to curve back toward itself with the attachment means unattached from the connection means and upon extension of the second section of the strap means out through the distal open end of the conduit means.

3. The medical device of claim 1 wherein the first section of the strap means extends along and through the conduit means and outwardly of the conduit means adjacent to the proximal portion of the conduit means to provide the manipulative means for moving the strap means along the inside passage of the conduit means.

4. The medical device of claim 1 wherein the manipulative means comprises drive rod means provided inside the conduit means and in a movable relationship with the inside passage thereof, the drive rod means having a proximal portion positioned near the proximal portion of the conduit means and wherein the first section of the strap means is connected to a distal portion of the drive rod means so that the drive rod means is manipulatable from the remote location to move the strap means along the inside passage of the conduit means.

5. The medical device of claim 1 wherein the first section of the strap means extends along and through the inside passage and outwardly of the conduit means adjacent to the proximal portion thereof to provide the manipulative means for moving the strap means along the inside passage of the conduit means, and wherein a second manipulative means comprises an attachment rod means provided inside the conduit means and in a movable relationship with the inside passage thereof, the attachment rod means having a proximal portion positioned near the proximal portion of the conduit means and wherein the attachment means of the strap means is releasibly attachable to a distal portion of the attachment rod means sewing as the strap connection means to thereby define the loop.

6. The medical device of claim 1 wherein the manipulative means comprises drive rod means provided inside the conduit means and in a movable relationship with the inside passage thereof, the drive rod means having a proximal portion positioned near the proximal portion of the conduit means, and wherein the first section of the strap means is connected to a distal portion of the drive rod means with the attachment means of the strap means releasibly attachable to a distal portion of the drive rod means serving as the strap connection means to define the loop so that the proximal portion of the drive rod means is manipulatable from the remote location to move the strap means along the inside passage of the conduit means to adjust a size of the loop extending from the distal open end of the conduit means.

7. The medical device of claim 1 wherein the manipulative means comprises drive rod means provided inside the conduit means and in a movable relationship with the inside passage thereof, the drive rod means having a proximal portion positioned near the proximal portion of the conduit means with the first section of the strap means connected to a distal portion of the drive rod means, a collar means surrounding a locking portion of the conduit means and in a movable relationship therewith, and a joining means for joining the collar means to the proximal portion of the drive rod means and in a manner allowing axial movement of the collar means along the proximal portion of the conduit means to move the drive rod means and associated strap means along the inside passage of the conduit means.

8. The medical device of claim 7 wherein the joining means comprises elongated connector means extending through the drive rod means and in a direction substantially normal to a first longitudinal axis of the drive rod means and wherein opposed ends of the connector means engage the collar means, the connector means being movable axially along a pair of diametrically opposed slots extending longitudinally along the proximal portion of the conduit means.

9. The medical device of claim 7 wherein the joining means further provides for rotational movement of the collar means and the drive rod means as a unit relative to the conduit means, the collar means supporting a locking means that can releasably contact the locking portion of the conduit means at an infinite number of annular locations around a second longitudinal axis of the conduct means to provide for locking and unlocking the drive rod means for preventing and allowing, respectively, movement of the strap means along the conduit means.

10. The medical device of claim 9 wherein the joining means comprises elongated connector means extending through the drive rod means in a direction substantially normal to a first longitudinal axis of the drive rod means and wherein opposed ends of the connector means are rotatably received in an inner annular groove provided on an inner wall of the collar means, the annular groove being concentric with the first longitudinal axis.

11. The medical device of claim 1 wherein the strap means has a second longitudinal axis and further comprising guide means provided on the conduit means for holding and directing movement of the strap means through the conduit means while preventing the strap means from rotating about the second longitudinal axis thereof relative to the inside passage of the conduit means.

12. The medical device of claim 11 wherein the guide means is provided at the distal portion of the conduit means and comprises a guide body having inner and outer end faces and a guide passage extending through the body between the end faces, and wherein the guide passage is elongated in a direction parallel to a plane of the width of the strap means and the guide passage is dimensioned and disposed so as to prevent the strap means from rotating about the second longitudinal axis thereof.

13. The medical device of claim 11 wherein the guide means comprises a guide body having an outer wall, and wherein the conduit means is provided with at least one inwardly projecting conduit protrusion that is removably receivable in a channel provided in the outer wall of the guide means to removably mount the guide means at the distal portion of the conduit means when the conduit protrusion is received in the channel.

14. The medical device of claim 13 wherein a pivotable tang portion of the guide means extends into the channel at a position spaced from a terminus portion thereof to lock the guide means to the conduit means at such time as the guide means has been manipulated to receive the conduit protrusion in the terminus portion of the channel of the guide means.

15. The medical device of claim 13 wherein the guide means further includes a guide passage that is elongated in a direction parallel to a plane of the width of the strap means and that is dimensioned and disposed so as to prevent the strap means from rotating about the second longitudinal axis thereof and wherein there are at least two sets of mating conduit protrusions and associated channels spaced along the sidewall of the conduit means and the outer wall of the guide means such that when the guide means is removably mounted at the distal portion of the conduit means, the elongated guide passage extending through the guide body is aligned along a predetermined plane with respect to a third longitudinal axis of the conduit means.

16. The medical device of claim 1 wherein the attachment means of the strap means comprises a strap opening extending through the thickness of the strap means with the strap connection means being associated with the conduit means and comprising a first post member extending from the conduit means, the first post member sized to mate with the strap opening to close the defined loop.

17. The medical device of claim 16 wherein the strap connection means includes a guard means that prevents the strap opening from releasing from its mated relationship with the first post member.

18. The medical device of claim 17 wherein the first post member comprising the strap connection means has a length between spaced apart first and second ends, the first end connected to the conduit means and the second end extending from the conduit means and spaced therefrom, and wherein the guard means comprises a second post member having a length between spaced apart ends, one end of the second post member connected to the conduit means with the other end thereof in an overlapping relationship with the second end of the first post member, wherein the second post member is in a resilient relationship with the first post member such that the post members are movable to a spaced relationship with respect to each other when the strap opening at the second section of the strap means is moved over the second end of the first post member, and wherein the strap opening is movable along the length of the first post member towards the first end thereof such that when the strap opening is clear of the second end of the first post member and the other end of the second post member, the resilient relationship between the first and second post members returns them to their overlapping relationship to attach the strap means to the strap connection means to close the defined loop with the guard means provided by the second post member preventing the strap means from releasing from the first post member.

19. The medical device of claim 1 wherein a locking means is provided on the conduit means, the locking means being accessible from the remote location and being movable to an enabled position to prevent movement of the strap means along the conduit means and wherein the locking means is movable to a disabled position to enable movement of the strap means along the inside passage of the conduit means.

20. The medical device of claim 19 wherein the locking means comprises a threaded member that is received in a threaded opening provided in the surrounding sidewall of the conduit means, the threaded member being rotatable in a first direction to contact either the manipulative means or the strap means inside the conduit means and thereby provide the enabled position for the locking means and wherein the threaded member is rotatable in a second direction to be removed from contact with either the manipulative means or the strap means inside the conduit means to thereby provide the disabled position for the locking means.

21. The medical device of claim 1 including a sealing means that seals between the inside of the conduit means and either the strap means or the manipulative means to prevent fluids present inside the body cavity from moving through the conduit means and past the sealing means when the distal portion of the conduit means is inserted into the body cavity, the sealing means allowing movement of the strap means and the manipulative means along the inside passage of the conduit means.

22. The medical device of claim 1 wherein the thickness of the strap means at the second section, spaced toward the first section from the attachment means, extends between a continuous inner surface and an outer surface with at least one recessed formation formed into the thickness from the inner surface and extending towards the outer surface to a depth through the thickness at least intermediate the inner and outer surfaces so that when the attachment means at the second section of the strap means is attached to the strap connection means to define the loop, the manipulative means is manipulatable to tighten the loop around the body organ and the recessed formation prevents the tightened loop from releasing from the body organ as the device is used to manipulate the body organ.

23. The medical device of claim 22 wherein the recessed formation comprises a plurality of openings extending through the thickness of the strap means and positioned at spaced locations along the loop to thereby prevent the tightened loop from releasing from the body organ.

24. The medical device of claim 23 wherein the openings providing the recessed formations are beveled.

25. The medical device of claim 24 wherein the beveled openings have a narrow opening portion facing inwardly of the loop.

26. The medical device of claim 1 wherein the conduit means, the strap means and the manipulative means comprise a kit for providing the medical device and wherein at least some of them are disposable.

27. The medical device of claim 26 wherein the strap means has a longitudinal axis and the kit further comprises a guide means positionable on the conduit means for preventing the strap means from rotating about the longitudinal axis thereof relative to the inside passage of the conduit means and wherein the guide means is disposable.

28. The medical device of claim 26 further comprising a sealing means that seals between the inside of the conduit means and either the strap means or the manipulative means to prevent fluids present inside the body cavity from moving through the conduit means to the proximal open end thereof when the distal portion of the conduit means is inserted into the body cavity, the sealing means allowing movement of the strap means and the manipulative means along the inside passage of the conduit means and wherein the sealing means is disposable.

29. The medical device of claim 26 further including a locking means that is positionable on the conduit means, the locking means being accessible from the remote 16cation and being movable to an enabled position to prevent movement of the strap means along the conduit means and wherein the locking means is movable to a disabled position to enable movement of the strap means along the inside passage of the conduit means and wherein the locking means is disposable.

30. A medical device that is insertable into a body cavity to hold and manipulate a body organ located therein from a remote location outside the cavity during a surgical procedure, which comprises:

a) elongated conduit means having surrounding sidewall providing an inside passage extending to proximal and distal portions having respective spaced apart open ends, wherein the proximal portion of the conduit means provides a handle means for inserting the distal portion into the body cavity and for manipulating the distal portion from the remote location;

b) flexible strap means having a width and a thickness so as to be in a movable relationship in the inside passage of the conduit means, wherein at least a portion of the strap means is extendable out through the distal open end of the conduit means, the strap means provided with an attachment means and having a first section and a second section and wherein the thickness of the strap means at the second section extends between a continuous inner surface and an outer surface with at least one recessed formation formed into the thickness from the inner surface and extending towards the outer surface to a depth through the thickness at least intermediate the inner and outer surfaces; and c) manipulative means operatively associated with the strap means and manipulatable from the remote location to move the strap means along the inside passage of the conduit means so that upon extension of at least the second section of the strap means out through the distal open end of the conduit means the attachment means is either initially in an unattached state and attachable to a strap connection means provided by the medical device or first detachable from the strap connection means and then reattachable thereto such that the attachment means is removably mated to the strap connection means with either the attachment means surrounding the strap connection means or the strap connection means surrounding the attachment means to thereby define a loop, and wherein the manipulative means is manipulatable to tighten the loop around the body organ and the recessed formation prevents the tightened loop from releasing from around the body organ as the device is used to manipulate the body organ.

31. The medical device of claim 30 wherein the manipulative means comprises a drive rod means provided inside the conduit means and in a movable relationship with the inside passage thereof, the drive rod means having a proximal portion positioned near the proximal portion of the conduit means and wherein the first section of the strap means is connected to a distal portion of the drive rod means so that the proximal portion of the drive rod means is manipulatable from the remote location to move the strap means along the inside passage of the conduit means, and wherein a second manipulative means comprises an attachment rod means provided inside the conduit means and in a movable relationship with the inside passage thereof, the attachment rod means having a second, proximal portion positioned near the proximal portion of the conduit means and wherein the attachment means of the strap means is releasibly attachable to a distal portion of the attachment rod means serving as the strap connection means to thereby define the loop.

32. The medical device of claim 30 wherein the strap means has a longitudinal axis and further comprising guide means provided on the conduit means for holding and directing movement of the strap means along and through the conduit means while preventing the strap means from rotating about the longitudinal axis thereof relative to the inside passage of the conduit means.

33. The medical device of claim 30 wherein a locking means is provided on the conduit means, the locking means being accessible from the remote location and being movable to an enabled position to prevent movement of the strap means along and through the conduit means and wherein the locking means is movable to a disabled position to enable movement of the strap means along the inside passage of the conduit means.

34. The medical device of claim 30 including a sealing means that seals between the inside of the conduit means and either the strap means or the manipulative means to prevent fluids present inside the body cavity from moving through the conduit means and past the sealing means when the distal portion of the conduit means is inserted into the body cavity, the sealing means allowing movement of the strap means and the manipulative means along the inside passage of the conduit means.

35. A medical device that is insertable into a body cavity during a surgical procedure to hold and manipulate a body organ from a remote location outside the body cavity, which comprises:
  a) elongated conduit means having a surrounding sidewall providing an inside passage and extending to proximal and distal portions having respective spaced apart open ends, wherein the proximal portion of the conduit means provides a handle means for inserting the distal portion into the body cavity and for manipulating the distal portion from the remote location;
  b) flexible strap means having a width so as to be in a movable relationship in the inside passage of the conduit means, and at least a portion of the strap means is extendable out through the distal open end of the conduit means, wherein the strap means includes a first section and a second section;
  c) first manipulative means provided by the first section of the strap means which extends along and through the inside passage and outwardly of the conduit means adjacent to the proximal portion thereof and being manipulatable from the remote location to move the strap means along the inside passage of the conduit means to extend at least the second section of the strap means out through the distal open end of the conduit means; and
  d) a second manipulative means comprising attachment rod means provided inside the conduit means and in a movable relationship with the inside passage thereof, the attachment rod means having a proximal portion positioned near the proximal portion of the conduit means and wherein the strap means is provided with an attachment means which upon extension of the second section of the strap means out through the distal open end of the conduit means is either initially in an unattached state and attachable to a strap connection means provided by a distal portion of the attachment rod means or first detachable from the strap connection means and then reattachable thereto such that the attachment means is removably mated to the strap connection means with either the attachment means surrounding the strap connection means or the strap connection means surrounding the attachment means to thereby define a loop comprising the strap means.

36. The medical device of claim 35 wherein the second section of the strap means is provided with memory-curved characteristics that cause the second section to curve back toward itself with the attachment means unattached from the connection means and upon extension of the second section of the strap means out through the distal open and of the conduit means.

37. The medical device of claim 36 wherein the thickness of the strap means at the second section, spaced toward the first section from the attachment means, extends between an inner surface and an outer surface with at least one recessed formation formed into the thickness from the inner surface and extending towards the outer face to a depth through the thickness at least intermediate the inner and outer surfaces so that when the attachment means of the strap means is attached to the strap connection means provided on the attachment rod means to define the loop, the first manipulative means is manipulatable to tighten the loop around the body organ and the recessed formation prevents the tightened loop from releasing from the body organ as the device is used to manipulate the body organ.

38. The medical device of claim 35 including a guide means provided on the conduit means for holding and directing movement of the strap means while preventing the strap means from rotating about a longitudinal axis of the strap means.

39. The medical device of claim 38 wherein the guide means is provided at the distal portion of the conduit means and comprises a guide body having inner and outer end faces and a guide passage extending through the body between the end faces, and wherein the guide passage is elongated in a direction parallel to the plane of the width of the strap means and is dimensioned and disposed so as to prevent the strap means from rotating about the longitudinal axis of the strap means.

40. The medical device of claim 35 wherein a locking means for the strap means is provided on the conduit means, the locking means being accessible from the remote location and being movable to an enabled position to prevent movement of the strap means along the conduit means and wherein the Locking means is movable to a disabled position to enable movement of the strap means along the inside passage of the conduit means.

41. The medical device of claim 35 including a sealing means that seals between the inside of the conduit means and at least one of the group consisting of the strap means, the first manipulative means and the second manipulative means to prevent fluids present inside the body cavity from moving through the conduit means and past the sealing means when the distal portion of the conduit means is inserted into the body cavity, the sealing means allowing movement of the strap means, the first manipulative means and the second manipulative means along the inside passage of the conduit means.

42. A medical device that is insertable into a body cavity during a surgical procedure to hold and manipulate a body organ from a remote location outside the body cavity, which comprises:
  a) elongated conduit means having a surrounding sidewall providing an inside passage extending to proximal and distal portions having respective spaced apart open ends, wherein the proximal portion of the conduit means provides a handle means for inserting the distal portion into the body cavity and for manipulating the distal portion from the remote location;

b) flexible holding means in a movable relationship in the inside passage of the conduit means, and at least a portion of the holding means is extendable out through the distal open end of the conduit means, wherein the holding means has a first section and a second section;

c) manipulative means operatively associated with the holding means and manipulatable from the remote location to move the holding means along the inside passage through the conduit meads to extend at least the second section of the holding means out through the distal open end of the conduit means, wherein the holding means is provided with an attachment means which upon extension of the second section of the holding means out through the distal open end of the conduit means is either initially in an unattached state and attachable to a holding connection means provided by the medical device or first detachable from the holding connection means and then reattachable thereto such that the attachment means is removably mated to the strap connection means with either the attachment means surrounding the strap connection means or the strap connection means surrounding the attachment means to thereby define a loop encircling the body organ and having relative rigidity in a plane normal to the loop; and d) sealing means provided inside the conduit means to seal between the inside of the conduit means and either the holding means or the manipulative means to thereby prevent fluids present inside the body cavity from moving through the conduit means and past the sealing means when the distal portion of the conduit means is inserted into the body cavity, the sealing means allowing movement of the holding means and the manipulative means along the conduit means.

43. The medical device of claim 42 wherein the second section of the holding means is provided with memory-curved characteristics that cause the second section to curve back toward itself with the attachment means unattached from the holding connection means and upon extension of the second section of the holding means out through the distal open end of the conduit means.

44. The medical device of claim 42 wherein the first section of the holding means extends along and through the inside passage and outwardly of the conduit means adjacent to the proximal portion thereof to provide the manipulative means for moving the holding means along the inside passage of the conduit means.

45. The medical device of claim 42 wherein a locking means for the holding means is provided on the conduit means, the locking means being accessible from the remote location and being movable to an enabled position to prevent movement of the holding means along the conduit means and wherein the locking means is movable to a disabled position to enable movement of the holding means along the inside passage of the conduit means.

46. A medical device that is insertable into a body cavity during a surgical procedure to hold and manipulate a body organ from a remote location outside the cavity, which comprises:

a) elongated conduit means having a surrounding sidewall providing an inside passage and extending to proximal and distal portions having respective spaced apart open ends, wherein the proximal portion of the conduit means provides a handle means for inserting the distal portion into the body cavity and for manipulating the distal portion from the remote location;

b) flexible strap means having a width and a thickness so as to be in a movable relationship in the inside passage of the conduit means, wherein at least a portion of the strap means is extendable out through the distal open end of the conduit means, the strap means having a first section and a second section;

c) manipulative means operatively associated with the strap means and manipulatable from the remote location to move the strap means along the inside passage of the conduit means to extend at least the second section of the strap means out through the distal open end of the conduit means, wherein the strap means is provided with an attachment means which upon extension of the second section of the strap means out through the distal open end of the conduit means is either initially in an unattached state and attachable to a connection means provided by the medical device or first detachable from the strap connection means and then reattachable thereto such that the attachment means is removably mated to the strap connection means with either the attachment means surrounding the strap connection means or the strap connection means surrounding the attachment means to thereby define a loop encircling the body organ and having relative rigidity in a plane normal to the loop; and d) sealing means provided inside the conduit means and in a sealing relationship therewith, wherein the sealing means meals between the inside of the conduit means and either the strap means or the manipulative means to prevent fluids present inside the body cavity from moving through the conduit means to the proximal open end thereof when the distal portion of the conduit means is inserted into the body cavity, and wherein upon formation of the loop, the handle means and the manipulative means are manipulatable from the remote location to position and tighten the defined loop around the body organ with the sealing means allowing movement of the strap means and the manipulative means along the conduit means.

47. The medical device of claim 46 wherein the second section of the strap means is provided with memory-curved characteristics that cause the second section to curve back toward itself with the attachment means unattached from the connector means and upon extension of the of the second section of the strap means out through the distal open end of the conduit means.

48. The medical device of claim 46 wherein the thickness of the strap means at the second section, spaced toward the first section from the attachment means, extends between a continuous inner surface and an outer surface with at least one recessed formation formed into the thickness from the inner surface and extending towards the outer surface to a depth through the thickness at least intermediate the inner and outer surfaces so that with the attachment means at the second section of the strap means attached to the strap connection means provided by the medical device to define the loop, the manipulative means is manipulatable to tighten the loop around the body organ and the recessed formation prevents the tightened loop from releasing from around the body organ as the device is used to manipulate the body organ.

49. The medical device of claim 46 wherein the first section of the strap means extends along and through the inside passage and outwardly of the conduit means adjacent to the proximal portion of the conduit means to provide the manipulative means for moving the strap means along the inside passage of the conduit means.

50. The medical device of claim 46 wherein the strap means has a longitudinal axis and further comprising guide means provided on the conduit means for preventing the strap means from rotating about the longitudinal axis thereof relative to the inside passage of the conduit means.

51. The medical device of claim 46 wherein a locking means for the strap means is provided on the conduit means, the locking means being accessible from the remote location and being movable to an enabled position to prevent movement of the strap means along the conduit means and wherein the locking means is movable to a disabled position to enable movement of the strap means along the inside passage of the conduit means.

* * * * *

UNITED STATES PATENT AND TRADEMARK OFFICE
CERTIFICATE OF CORRECTION

PATENT NO. : 5,613,973
DATED : March 25, 1997
INVENTOR(S) : Robert C. Jackson et al It is certified that error appears in the above-indentified patent and that said Letters Patent is hereby corrected as shown below:

```
Title page, item [54], and col. 1, line 1, should read--LAPAROSCOPIC--.
Col.  1, line 15 - delete "2nd" and insert --and--.
Col.  6, line  1 - delete "f" and insert --of--.
Col. 20, line 61 - delete "sewing" and insert --serving--.
Col. 24, line  3 - delete "16cation" and insert --location--.
Col. 28, line 31 - delete "meals" and insert --seals--.
```

Signed and Sealed this

First Day of July, 1997

Attest:

BRUCE LEHMAN

*Attesting Officer*     *Commissioner of Patents and Trademarks*